(12) United States Patent
Ide et al.

(10) Patent No.: US 10,010,252 B2
(45) Date of Patent: Jul. 3, 2018

(54) CIRCULATORY DYNAMICS MEASUREMENT APPARATUS

(75) Inventors: Kazuhiro Ide, Osaka (JP); Masato Izumikawa, Shiga (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 565 days.

(21) Appl. No.: 14/238,395

(22) PCT Filed: Aug. 30, 2012

(86) PCT No.: PCT/JP2012/005481
§ 371 (c)(1),
(2), (4) Date: Feb. 11, 2014

(87) PCT Pub. No.: WO2013/057866
PCT Pub. Date: Apr. 25, 2013

(65) Prior Publication Data
US 2014/0194755 A1    Jul. 10, 2014

(30) Foreign Application Priority Data

Oct. 19, 2011  (JP) .................................. 2011-230133
Apr. 24, 2012  (JP) .................................. 2012-099269

(51) Int. Cl.
*A61B 5/02*      (2006.01)
*A61B 5/0225*    (2006.01)
(Continued)

(52) U.S. Cl.
CPC ........ *A61B 5/0225* (2013.01); *A61B 5/02007* (2013.01); *A61B 5/6843* (2013.01);
(Continued)

(58) Field of Classification Search
CPC ..... A61B 5/0225; A61B 5/742; A61B 5/7275; A61B 5/02007; A61B 5/6843; A61B 5/02116; A61B 5/02225
See application file for complete search history.

(56) References Cited

U.S. PATENT DOCUMENTS 5,836,884 A * 11/1998 Chio .................. A61B 5/02007
600/485
2003/0083580 A1   5/2003 Tampo et al.
(Continued)

FOREIGN PATENT DOCUMENTS

CN    1551742 A      12/2004
EP    1 715 429 A1   10/2006
(Continued)

OTHER PUBLICATIONS

Fowkes, F. "Ankle Brachial Index Combined with Framingham Risk Score to Predict Cardiovascular Events and Mortality: A Meta-analysis." Journal of the American Medical Association. Jul. 9, 2008. 300(2); pp. 197-208.*
(Continued)

*Primary Examiner* — Tiffany Weston
(74) *Attorney, Agent, or Firm* — McDermott Will & Emery LLP

(57) ABSTRACT

The circulatory dynamics measurement apparatus comprises: a blood pressure-computing unit, which calculates the maximum blood pressure value (SYS); a vascular sclerosis-computing unit, which calculates the vascular sclerosis index (VSI); and a display unit for displaying a graph having a horizontal axis that represents the maximum blood pressure and a vertical axis that represents the vascular sclerosis index. The display unit displays the position determined by (Continued)

the calculated maximum blood pressure value and the calculated vascular sclerosis index in the plotting area of the graph.

13 Claims, 10 Drawing Sheets

(51) Int. Cl.
*A61B 5/00* (2006.01)
*A61B 5/021* (2006.01)
*A61B 5/022* (2006.01)

(52) U.S. Cl.
CPC ............ *A61B 5/7275* (2013.01); *A61B 5/742* (2013.01); *A61B 5/02116* (2013.01); *A61B 5/02225* (2013.01)

(56) References Cited

U.S. PATENT DOCUMENTS

| | | |
|---|---|---|
| 2003/0167014 A1 | 9/2003 | Ogura |
| 2004/0167414 A1* | 8/2004 | Tanabe .................... A61B 5/02 600/500 |
| 2004/0199273 A1 | 10/2004 | de Theije |
| 2005/0038327 A1 | 2/2005 | Tanaka et al. |
| 2005/0256412 A1 | 11/2005 | Shimazu et al. |
| 2006/0258944 A1 | 11/2006 | Takahashi et al. |
| 2007/0004985 A1 | 1/2007 | Suzuki et al. |
| 2008/0051838 A1 | 2/2008 | Shuros et al. |
| 2009/0005703 A1 | 1/2009 | Fasciano |
| 2009/0259131 A1 | 10/2009 | Tsuji et al. |
| 2009/0306523 A1 | 12/2009 | Saito et al. |
| 2010/0017182 A1 | 1/2010 | Voros et al. |
| 2010/0204591 A1 | 8/2010 | Hatib et al. |
| 2012/0157863 A1* | 6/2012 | Ide ........................ A61B 5/021 600/501 |
| 2012/0296382 A1 | 11/2012 | Shuros et al. |

FOREIGN PATENT DOCUMENTS

| | | | |
|---|---|---|---|
| EP | 1 733 679 A2 | 12/2006 | |
| EP | 2 011 435 A2 | 1/2009 | |
| EP | 2 047 793 A1 | 4/2009 | |
| EP | 2 110 074 A1 | 10/2009 | |
| JP | 09-506536 A | 6/1997 | |
| JP | 2938238 B2 | 8/1999 | |
| JP | 11-332837 A | 12/1999 | |
| JP | 2000-217796 A | 8/2000 | |
| JP | 2001-104258 A | 4/2001 | |
| JP | 2003-126054 A | 5/2003 | |
| JP | 2003-250769 A | 9/2003 | |
| JP | 2004-195204 A | 7/2004 | |
| JP | 2005-278708 * | 10/2005 | ........... A61B 5/0245 |
| JP | 2005-278708 A | 10/2005 | |
| JP | 2006-006893 A | 1/2006 | |
| JP | 2006-034368 A | 2/2006 | |
| JP | 2007-135966 A | 6/2007 | |
| JP | 2011-029958 A | 2/2011 | |
| JP | 5629600 B2 | 11/2014 | |
| TW | 200533317 A | 10/2005 | |
| WO | 2010/091055 A2 | 8/2010 | |

OTHER PUBLICATIONS

International Preliminary Examination Report on Patentability issued in International Application No. PCT/JP2012/005481 dated Apr. 22, 2014.
Taiwanese Office Action issued in Taiwanese Application No. 101134167 dated Nov. 13, 2013, w/English translation.
Chinese Office Action dated Jan. 30, 2015 issued in Chinese Patent Application No. 201280041970.5 (English translation).
International Search Report issued in International Application No. PCT/JP2012/005481 dated Oct. 23, 2012, with English Translation.
Extended European Search Report issued in European Patent Application No. 12842270.6 dated Feb. 17, 2015.
Japanese Office Action dated Mar. 10, 2015 issued in Japanese Patent Application No. 2012-099269 (with English translation).

* cited by examiner

CIRCULATORY DYNAMICS MEASUREMENT APPARATUS

RELATED APPLICATIONS

This application is the U.S. National Phase under 35 U.S.C. § 371 of International Application No. PCT/JP2012/005481, filed on Aug. 30, 2012, which in turn claims the benefit of Japanese Application No. 2011-230133, filed on Oct. 19, 2011, and Japanese Application No. 2012-099269, filed Apr. 24, 2012, the disclosures of which are incorporated by reference herein.

TECHNICAL FIELD

The present invention relates to a circulatory dynamics measurement apparatus that measures the condition of a living body based on a pulse wave obtained from the living body.

BACKGROUND ART

Lifestyle-related diseases have been increasing over these recent years. Lifestyle-related diseases are associated with circulatory dynamics such as the heart and blood vessels of the body. In one method for diagnosing arteriosclerosis, cuffs are attached to the two arms and two, pulse waves are detected while keeping a predetermined pressure applied to the locations where the cuffs are attached for a certain time, and a pulse wave propagation velocity PWV is calculated from the pulse wave propagation time between two locations and the distance between the two areas to measure the blood vessel hardness as the circulatory dynamics (patent document 1). In another method, the blood vessel hardness is measured based on a CAVI (cardio ankle vascular index) that is less likely to be dependent on the blood pressure than the pulse wave propagation velocity PWV (patent document 2). However, in the conventional testing methods, the measured subject needs to lie on a bed and have the four limbs constrained. Further, the measurement apparatus that performs the conventional testing method is expensive and cannot be easily used in general households.

Thus, a method that can be used in general households, specifically, a technique for measuring the blood vessel hardness from the pulse wave value obtained while measuring the blood pressure at the upper arm has been proposed (for example, refer to patent documents 3 to 5). In the measuring method of patent document 3, a compression pressure is raised to a target pressure and the compression pressure is then gradually reduced. As the pressure decreases, the amplitude value of the pulse wave is sequentially detected to obtain the relationship of the compression pressure and the amplitude value of the pulse wave. It is known that the relationship of the compression pressure and the amplitude value of the pulse wave may be shown by an envelope in which the amplitude value of the pulse wave is maximal when the compression pressure substantially conforms to the average blood pressure value. An inclination angle θ of a line in the envelope connecting the point corresponding to the systolic blood pressure value and the point corresponding to the amplitude value of 63.2% of the maximum amplitude value is obtained to determine the degree of arteriosclerosis of the measured subject in accordance with the inclination angle θ.

In the measuring method of patent document 4, a signal in which a pulse wave amplitude component is superimposed on the cuff pressure is time differentiated and the maximum value for each heartbeat is plotted to form the envelope. Then, the pressure width corresponding to the value of the time differentiated signal is used to determine the degree of arteriosclerosis of the measured subject.

In the measuring method of patent document 5, the amplitude values of the pulse waves are plotted relative to the compression pressure to form an envelope, the compression pressure is divided to a high pressure side and a low pressure side using the maximum amplitude value as a reference, and a plurality of pressure values at the high pressure side and the low pressure side of a predetermined amplitude value is used to determine the degree of arteriosclerosis of the measured subject.

The relationship of the amplitude value of the pulse wave and the compression pressure forms an envelope because the change in blood vessel volume is small when the difference is large between the blood pressure and the pressure applied from the exterior to the blood vessel, or the so-called blood vessel interior-exterior pressure difference, and because the change in blood vessel volume is large when the blood vessel interior-exterior pressure difference is around zero. This is known as a pressure-volume curve of the blood vessel, and the inclination of the pressure-volume curve is an index representing the hardness of the blood vessel.

PRIOR ART DOCUMENTS

Patent Documents

Patent Document 1: Japanese Laid-Open Patent Publication No. 2003-126054
Patent Document 2: Japanese Laid-Open Patent Publication No. 2006-6893
Patent Document 3: Japanese Patent No. 2938238
Patent Document 4: Japanese Laid-Open Patent Publication No. 2001-104258
Patent Document 5: Japanese Laid-Open Patent Publication No. 2005-278708

SUMMARY OF THE INVENTION

In a conventional measurement apparatus such as an automatic electronic sphygmomanometer that allows for the blood pressure to be easily measured at home, the blood pressure and the blood vessel hardness are independently displayed. With regard to the blood pressure, there is a conventional measurement apparatus that shows the systolic blood pressure and the diastolic blood pressure in a two-dimensional graph. However, there are no measurement apparatuses that visually show the relationship of the blood pressure and the blood vessel hardness.

More specifically, the blood pressure represents the pumping function of the heart, and the blood vessel hardness represents the flexibility of the blood vessel. Thus, the blood pressure and the blood vessel hardness are different parameters. However, when the conventional measurement apparatus is used at home where there are no healthcare professionals such as a doctor, it would be difficult for the measured subject, who is not a healthcare professional, to understand the condition indicated by the blood pressure and the blood vessel hardness shown on the measurement apparatus.

It is an object of the present invention to provide a circulatory dynamics measurement apparatus that visually shows the relationship of the blood pressure and the circulatory dynamics.

One aspect of the present invention is a circulatory dynamics measurement apparatus including a pressure application member that compresses a predetermined region of a body of a measured subject. A pressure detection unit detects a compression pressure of the pressure application member. A pressure control unit changes the compression pressure of the pressure application member. A storage unit stores a pulse wave value, which is related to a magnitude of a pulse wave generated at the predetermined region based on the compression pressure, and a compression pressure, which is detected by the pressure detection unit, in association with each other as the pressure control unit changes the compression pressure. A calculation unit calculates a non-blood pressure circulatory dynamics index and at least either one of a systolic blood pressure and a diastolic blood pressure and using the compression pressure and the pulse wave value that are associated with each other. A display unit shows a graph including an axis indicating blood pressure and an axis indicating a non-blood pressure circulatory dynamics index. The display unit shows in a plotting area of the graph a position defined by the calculated blood pressure and the calculated non-blood pressure circulatory dynamics index.

A further aspect of the present invention is a circulatory dynamics measurement apparatus including a pressure application member that compresses a predetermined region of a body of a measured subject. A pressure detection unit detects a compression pressure of the pressure application member. A pressure control unit changes the compression pressure of the pressure application member. A storage unit stores a pulse wave value, which is related to a magnitude of a pulse wave generated at the predetermined region based on the compression pressure, and a compression pressure, which is detected by the pressure detection unit, in association with each other as the pressure control unit changes the compression pressure. A calculation unit calculates a non-blood pressure circulatory dynamics index and at least either one of a systolic blood pressure and a diastolic blood pressure using the compression pressure and the pulse wave value that are associated with each other. A determination unit determines whether or not the calculated blood pressure exceeds a blood pressure reference value and determines whether or not the calculated non-blood pressure circulatory dynamics index exceeds a non-blood pressure circulatory dynamics index reference value to generate a determination result of the circulatory dynamics. A display unit displays the determination result of the determination unit.

In one example, the display unit shows a blood pressure reference value and a non-blood pressure circulatory dynamics index reference in the graph to divide a plotting area of the graph into a plurality of sub-regions.

In one example, the blood pressure reference value and the non-blood pressure circulatory dynamics index reference value are set in accordance with physical information of the measured subject.

In one example, the display unit shows a most recent measurement result and a past measurement result in the graph.

In one example, the non-blood pressure circulatory dynamics index includes at least a blood vessel hardness index.

In one example, the calculation unit calculates the blood vessel hardness index based on an envelope formed by a cumulatively added pulse wave value generated by cumulatively adding the pulse wave values and the compression pressure associated with the pulse wave value.

In one example, the blood vessel hardness index is a value corrected by a blood pressure.

In one example, the calculation unit calculates a cumulatively added pulse wave value for each compression pressure by cumulatively adding the pulse wave values acquired continuously or intermittently acquired as the compression pressure changes in a detection order of the corresponding compression pressures, obtains a characteristic line generated by plotting the cumulatively added pulse wave values in the detection order of the corresponding compression pressures, and calculates the blood vessel hardness index based on at least one of a ratio of a cumulatively added pulse wave value corresponding to a predetermined first compression pressure in the characteristic line and a cumulatively added pulse wave value corresponding to a second compression pressure that differs from the first compression pressure value in the characteristic line, and a ratio of a compression pressure corresponding to a predetermined first cumulatively added pulse wave value in the characteristic line and a compression pressure corresponding to a second cumulatively added pulse wave value that differs from the first cumulatively added pulse wave value in the characteristic line.

In one example, the calculation unit calculates a cumulatively added pulse wave value for each compression pressure by cumulatively adding the pulse wave values acquired continuously or intermittently acquired as the compression pressure changes in a detection order of the corresponding compression pressures, divides each cumulatively added pulse wave value by a total cumulatively added pulse wave value generated by cumulatively adding all of the pulse wave values acquired during a blood pressure measurement to calculate a cumulatively added pulse wave value ratio for each compression pressure, obtains a characteristic line generated by plotting the cumulatively added pulse wave value ratio in the detection order of the corresponding compression pressure, and calculates the blood vessel hardness index based on at least one of a ratio of the cumulatively added pulse wave value ratio corresponding to a predetermined first compression pressure in the characteristic line and the cumulatively added pulse wave value ratio corresponding to a second compression pressure that differs from the first compression pressure in the characteristic line, and a ratio of a compression pressure corresponding to a predetermined first cumulatively added pulse wave value ratio in the characteristic line and a compression pressure corresponding to a predetermined second cumulatively added pulse wave value ratio in the characteristic line.

In one example, the blood vessel hardness index is corrected in accordance with physical information of a measured subject.

In one example, the blood vessel hardness index is corrected in accordance with sex.

One example of the circulatory dynamics measurement apparatus includes a condition determination unit that determines whether or not the calculated blood pressure exceeds a blood pressure reference value and determines whether or not the calculated non-blood pressure circulatory dynamics index exceeds the non-blood pressure circulatory dynamics index reference value to generate a determination result of the circulatory dynamics. The display unit shows a message or an image corresponding to the determination result of the condition determination unit.

In one example, the calculation unit calculates the blood pressure as a first circulatory dynamics index, the non-blood pressure circulatory dynamics index as a second circulatory dynamics index, and a third circulatory dynamics index that differs from the first and second circulatory dynamics indices. The display unit shows a graph including an axis representing the blood pressure and an axis representing the non-blood pressure circulatory dynamics index, and a mark at a position defined by the blood pressure and the non-blood pressure circulatory dynamics index in a plotting area of the graph. The display unit changes a display mode of the mark in accordance with a value of the third circulatory dynamics index.

In one example, the third circulatory dynamics index is at least one selected from a Framingham score, an eGFR, or an intima-media thickness of a carotid artery.

Effect of the Invention

In the present invention, the circulatory dynamics measurement apparatus visually shows the relationship of the blood pressure and the circulatory dynamics.

EMBODIMENTS OF THE INVENTION

First Embodiment

A circulatory dynamics measurement apparatus according to a first embodiment of the present invention will now be described.

Figure 1:
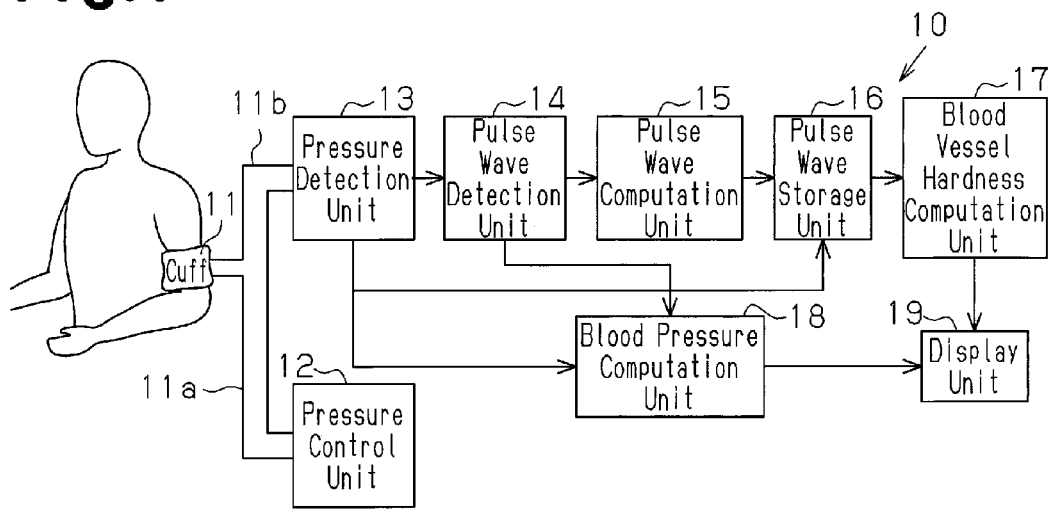
FIG. 1 is a block diagram of a circulatory function measurement apparatus according to a first embodiment of the present invention.

As shown in FIG. 1, a circulatory dynamics measurement apparatus 10 includes a cuff 11 serving as a pressure application member for compressing a predetermined region of a body of a measured subject. The predetermined region of the measured subject is, for example, an upper arm. The cuff 11 is wound around and attached to the upper arm of the measured subject when measuring the blood pressure and the blood vessel hardness, which is one type of a circulatory dynamics other than the blood pressure, of the measured subject. The cuff 11 compresses the upper arm (brachial artery) of the measured subject as the interior air pressure (compression pressure) changes when attached to the upper arm of the measured subject. In a non-restrictive example, the cuff 11 may be a belt-shaped member including a rubber pressurizing bag.

The cuff 11 is connected to a pressure control unit 12 that changes the compression pressure of the cuff 11. The pressure control unit 12 may include a pressurization pump (not shown), which is capable of feeding gas under pressure to the cuff 11 through a tube 11a, and a discharge valve (not shown), which discharges the gas from the cuff 11. The pressure control unit 12 controls the pressurization pump and the discharge valve to change the compression pressure of the cuff 11.

The cuff 11 is connected to a pressure detection unit 13 that detects the compression pressure of the cuff 11 through a tube 11b. The pressure detection unit 13 is connected to a pulse wave detection unit 14. The pulse wave detection unit 14 detects a pulse wave value, which is related to the magnitude of the pulse wave generated at the upper arm when the pressure control unit 12 changes the compression pressure, in association with the compression pressure. The pressure detection unit 13 includes a pressure sensor (not shown) and an A/D converter (not shown). The pressure detection unit 13 converts the compression pressure of the cuff 11 detected by the pressure sensor to a pressure signal formed by a digital signal with the A/D converter, and provides the pressure signal to the pulse wave detection unit 14. The pulse wave detection unit 14 includes a filter circuit (not shown) and generates a pulse wave signal by removing a predetermined frequency component such as a DC component from the pressure signal of the pressure detection unit 13 with the filter circuit, and detects the amplitude value of the pulse wave (detected pulse wave) from the generated pulse wave signal. The amplitude value of the pulse wave may be referred to as the height of the pulse wave.

A pulse wave computation unit 15 is connected to the pulse wave detection unit 14. The pulse wave computation unit 15 cumulatively adds the amplitude values of the pulse waves provided from the pulse wave detection unit 14 to generate a cumulatively added pulse wave value. The cumulatively added pulse wave value includes a cumulatively added value of the amplitudes of the pulse waves detected at various compression pressures. The pressure detection unit 13 and the pulse wave computation unit 15 are connected to a pulse wave storage unit 16 and respectively provide the compression pressure and the cumulatively added pulse wave value to the pulse wave storage unit 16. The pulse wave storage unit 16 stores the provided compression pressure and the cumulatively added pulse wave value in association with each other. A blood vessel hardness computation unit 17 is connected to the pulse wave storage unit 16 and reads the compression pressure and the cumulatively added pulse wave value associated with the compression pressure from the pulse wave storage unit 16. Further, the blood vessel hardness computation unit 17 calculates a blood vessel hardness index indicating the hardness of the brachial artery (hereinafter may be referred to as "blood vessel hardness"), which is one of the circulatory dynamics, with a predetermined algorithm based on the read compression pressure and cumulatively added pulse wave value. Then, the blood vessel hardness computation unit 17 provides the blood vessel hardness index to a display unit 19. The blood vessel hardness computation unit 17 may include a ROM that stores a program for measuring and computing the blood vessel hardness of the measured subject, a program for controlling each unit of the circulatory dynamics measurement apparatus 10, and the like, a RAM that temporarily saves data generated during and after the execution of a program, a CPU that reads and executes various types of programs from the ROM, and the like.

As shown in FIG. 1, the pressure detection unit 13 and the pulse wave detection unit 14 are each connected to a blood pressure computation unit 18. The blood pressure computation unit 18 calculates a systolic blood pressure and a diastolic blood pressure of the measured subject with a predetermined algorithm such as the oscillometric method from the compression pressure detected by the pressure detection unit 13 and the amplitude value of the pulse wave detected by the pulse wave detection unit 14. Then, the blood pressure computation unit 18 provides the systolic blood pressure and the diastolic blood pressure to the display unit 19. The display unit 19, which is connected to the blood vessel hardness computation unit 17 and the blood pressure computation unit 18, shows the blood vessel hardness index and the blood pressure respectively provided from the blood vessel hardness computation unit 17 and the blood pressure computation unit 18.

The blood vessel hardness computation unit 17 and the blood pressure computation unit 18 are included in a calculation unit. The blood pressure may be referred to as a first circulatory dynamics index. The blood vessel hardness index is an example of a second circulatory dynamics index and a non-blood pressure circulatory dynamics index.

The operation of the circulatory dynamics measurement apparatus 10 will now be described.

Figure 2:
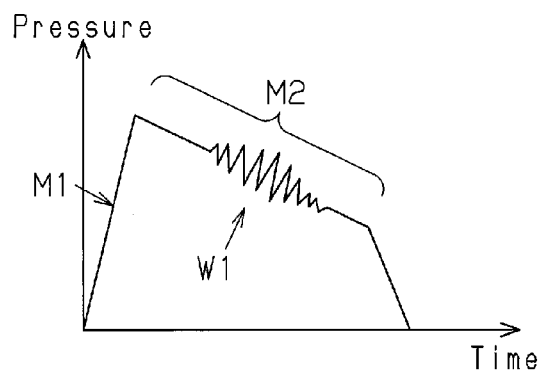
FIG. 2 is a graph showing changes in the compression pressure from when starting the compression of a brachial artery to when ending the compression.

As shown in FIG. 1, when the cuff 11 attached to the upper arm of the measured subject, the pressure control unit 12 raises the compression pressure of the cuff 11 so that the brachial artery of the measured subject is gradually compressed by the cuff 11. Specifically, as shown in FIG. 2, the pressure control unit 12 suddenly raises the compression pressure of the cuff 11 to a predetermined pressure value (indicated by line M1) that is higher than the expected systolic blood pressure of the measured subject.

The pressure control unit 12 then gradually reduces the compression pressure from the predetermined pressure value at a low speed (indicated by line M2). The pressure control unit 12 discharges air from the cuff 11 when the compression pressure reaches a predetermined pressure value that is lower than the expected diastolic blood pressure of the measured subject during the low speed pressure reduction. This readily cancels the compression of the brachial artery of the measured subject with the cuff 11.

Figure 3:
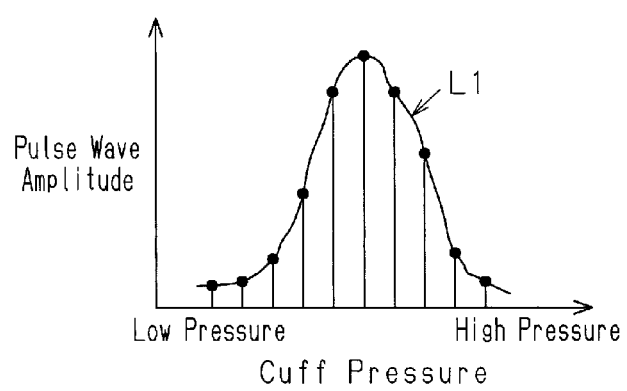
FIG. 3 is a graph showing the relationship of a cuff pressure and the amplitude value of a detected pulse wave.

When the compression pressure of the cuff 11 changes, in particular, during the low speed pressure reduction, the pulsation of the heart generates a pulse wave W1. The amplitude value of the pulse wave W1 is continuously or intermittently detected by the pulse wave detection unit 14. The relationship of the amplitude value of the pulse wave W1 and the compression pressure of the cuff 11 will now be described with reference to FIG. 3. The detected amplitude value X of the pulse wave W1 changes in accordance with the compression pressure P of the cuff 11 as shown by an envelope L1 in FIG. 3. Specifically, as the compression pressure P of the cuff 11 increases from the low pressure side toward the high pressure side, the amplitude value X of the pulse wave W1 first gradually rises and then suddenly rises. The amplitude value X takes a maximum value at a predetermined compression pressure, which corresponds to the compression pressure at an average blood pressure, and then decreases. In FIG. 3, in the amplitude values having a magnitude of a predetermined ratio relative to the maximum amplitude value of the pulse wave W1, the cuff pressure corresponding to an intersection at the high pressure side indicates a systolic blood pressure value SYS, and the cuff pressure corresponding to an intersection at the low pressure side indicates a diastolic blood pressure value DIA. The blood pressure computation unit 18 computes the systolic blood pressure value SYS and the diastolic blood pressure value DIA in accordance with the envelope L1 and the amplitude value having a magnitude of a predetermined ratio relative to the maximum amplitude value of the pulse wave W1.

Figure 4A:
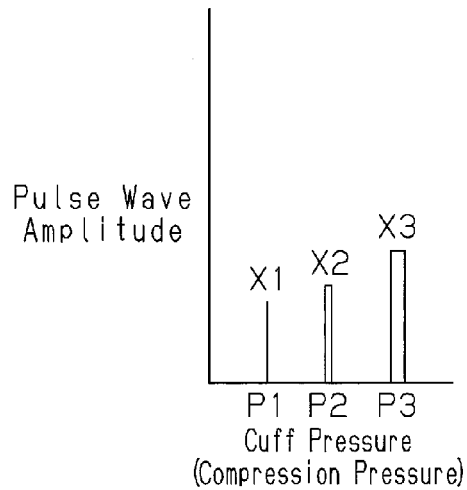
FIG. 4A is a graph showing a measurement example of the amplitude of the detected pulse wave corresponding to the cuff pressure.
Figure 4B:
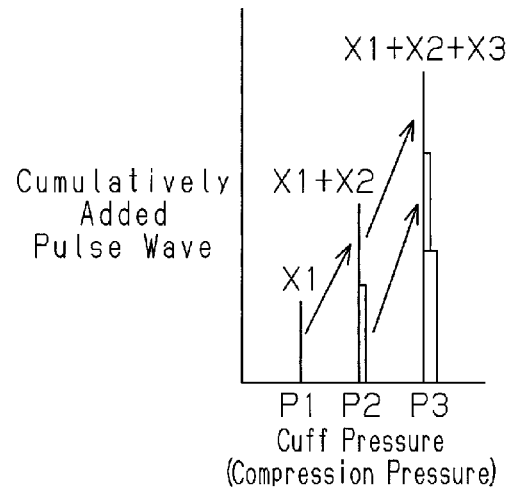
FIG. 4B is a graph showing a cumulatively added pulse wave corresponding to the amplitude of the detected pulse wave of FIG. 4A.

The pulse wave computation unit 15 calculates the cumulatively added pulse wave value by cumulatively adding the amplitude values X of the pulse wave W1, and stores the cumulatively added pulse wave value in the pulse wave storage unit 16 in association with the compression pressure P. In the example shown in FIG. 4A, the pulse wave detection unit 14 detects the amplitude value X1 of the pulse wave W1 at compression pressure P1, the amplitude value X2 of the pulse wave W1 at compression pressure P2, and the amplitude value X3 of the pulse wave W1 at compression pressure P3. In this example, the compression pressure P3 is the largest in the order of compression pressure P1<compression pressure P2<compression pressure P3. In this case, as shown in FIG. 4B, the pulse wave computation unit 15 calculates the cumulatively added pulse wave value X1 at compression pressure P1, calculates the cumulatively added pulse wave value X1+X2 at compression pressure P2, and calculates the cumulatively added pulse wave values X1+X2+X3 at compression pressure P3. The pulse wave computation unit 15 thus continuously or intermittently acquires the amplitude value of the pulse wave W1 while the compression pressure is changing, and cumulatively adds the amplitude values of the pulse wave W1. The pulse wave computation unit 15 stores the amplitude value of the pulse wave W1 from when the compression of the brachial artery starts to when the compression ends. Then, the pulse wave computation unit 15 calculates the cumulatively added pulse wave value in order from the low pressure based on the stored amplitude value and the compression pressure. The pulse wave storage unit 16 stores the calculated cumulatively added pulse wave value in association with the compression pressure.

Figure 5:
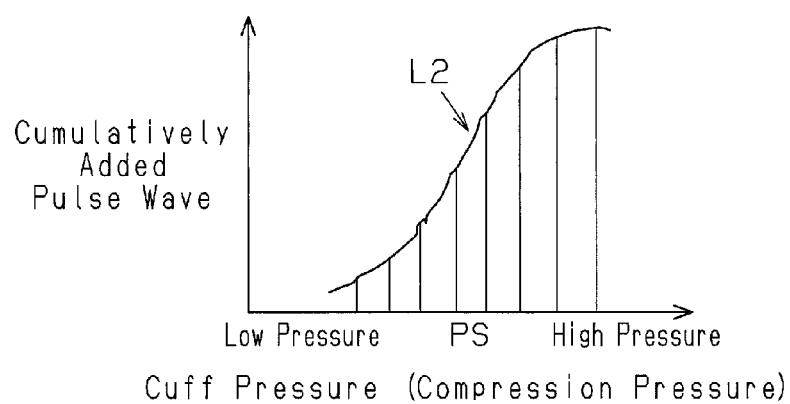
FIG. 5 is a diagram showing a characteristic line representing the relationship of the cumulatively added pulse wave value and the cuff pressure.

The cumulatively added pulse wave value and the associated compression pressure form a characteristic line L2 shown in FIG. 5. In other words, as the compression pressure of the cuff 11 increases, the calculated cumulatively added pulse wave value first gradually rises and then suddenly rises when the compression pressure of the cuff 11 reaches a predetermined compression pressure Ps. The rising degree gradually becomes smaller as the compression pressure of the cuff 11 becomes higher than the predetermined compression pressure Ps. The predetermined compression pressure Ps is the compression pressure when the cumulatively added pulse wave value is increased to the highest level.

Figure 6:
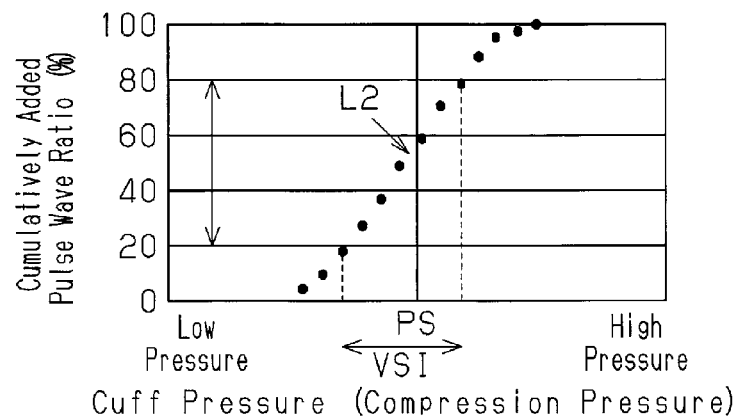
FIG. 6 is a graph showing the relationship of the cumulatively added pulse wave value ratio and the cuff pressure.
Figure 7:
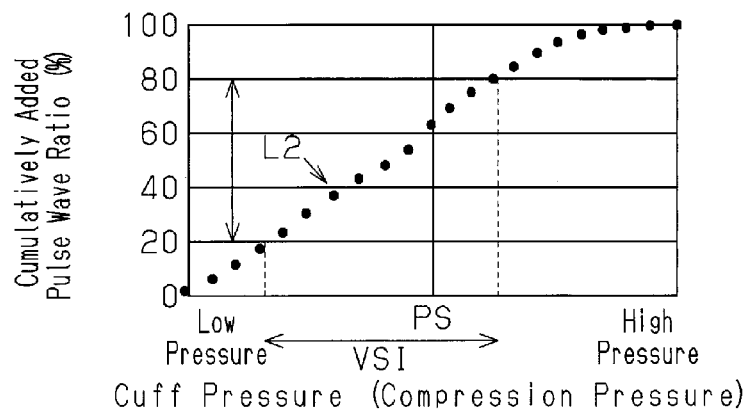
FIG. 7 is a graph showing the relationship of the cumulatively added pulse wave value ratio and the cuff pressure.

The blood vessel hardness computation unit 17 computes the blood vessel hardness in accordance with a predetermined algorithm from the relationship of the cumulatively added pulse wave value and the compression pressure stored in the pulse wave storage unit 16. Specifically, the blood vessel hardness computation unit 17 calculates a standardized cumulatively added pulse wave value ratio for each compression pressure by setting the total cumulatively added pulse wave value, which is generated by cumulatively adding the amplitude values of all of the pulse waves obtained during the blood pressure measurement, as 100%. That is, the blood vessel hardness computation unit 17 calculates, for each compression pressure, the cumulatively added pulse wave value ratio indicating the percentage of the cumulatively added pulse wave value associated with each compression pressure when the total cumulatively added pulse wave value generated by cumulatively adding the amplitude values of all of the pulse waves obtained during the blood pressure measurement is 100%. The blood vessel hardness computation unit 17 obtains the width of the compression pressure that changes during a period corresponding to a range (e.g., 20% to 80%) of the cumulatively added pulse wave value ratio determined in advance in the calculated cumulatively added pulse wave value ratio. Then, the blood vessel hardness computation unit 17 provides the obtained width of the compression pressure to the display unit 19 as a blood vessel hardness index VSI. The value of the blood vessel hardness index VSI is small if the blood vessel is soft, and the value of the blood vessel hardness index VSI is large if the blood vessel is hard. For example, FIG. 6 shows the blood vessel hardness index VSI corresponding to a soft blood vessel, and FIG. 7 shows the blood vessel hardness index VSI corresponding to a hard blood vessel. The blood vessel hardness index VSI corresponds to the amount of work of the compression pressure necessary for compressing the blood vessel. For example, the amount of work of the compression pressure necessary for compressing a soft blood vessel is small, and the amount of work of the compression pressure necessary for compressing a hard blood vessel is large.

The display of the systolic blood pressure value SYS calculated by the blood pressure computation unit 18 and the blood vessel hardness index VSI calculated by the blood vessel hardness computation unit 17 will now be described.

Figure 8:
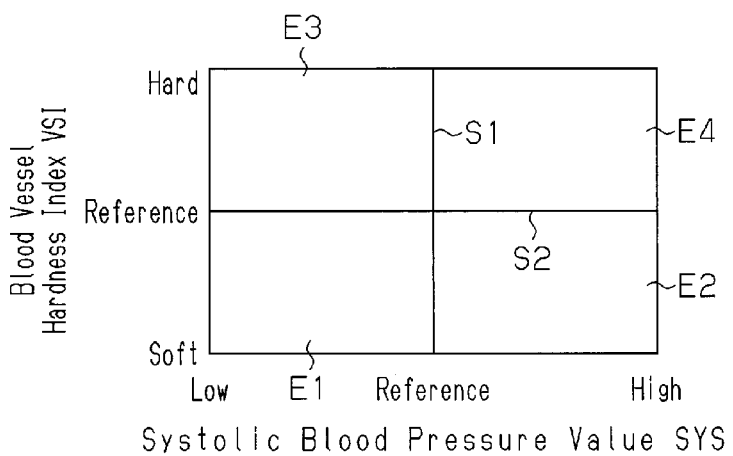
FIG. 8 is a schematic diagram of a graph shown on a display unit.

As shown in FIG. 8, the display unit 19 shows a graph including a horizontal axis, which indicates the systolic blood pressure value SYS, and a vertical axis, which indicates the blood vessel hardness index VSI. In one example, the graph is a scatter diagram. The display unit 19 plots a position (also referred to as resulting position or measurement point) defined by the systolic blood pressure value SYS calculated by the blood pressure computation unit 18 and the blood vessel hardness index VSI calculated by the blood vessel hardness computation unit 17. The measured subject can recognize the relationship of the systolic blood pressure value SYS and the blood vessel hardness index VSI at a glance from the resulting position plotted in the plotting area. This allows the condition of the measured subject to be recognized.

A systolic blood pressure reference value S1 is shown at a central position of the horizontal axis. A blood vessel hardness reference value S2 is shown at a central position of the vertical axis. The systolic blood pressure reference value S1 divides the plotting area of the graph into two, namely, the left half and the right half. The blood vessel hardness reference value S2 divides the plotting area of the graph into two, namely, the upper half and the lower half. Therefore, the plotting area of the graph is divided into sub-regions E1 to E4 by the reference values S1 and S2.

For example, if the resulting position is plotted in the lower left sub-region E1, the systolic blood pressure value SYS is lower than the reference value S1 and the blood vessel hardness index VSI is lower than the reference value S2. Thus, the measured subject can determine that the measurement result of the circulatory dynamics measurement apparatus 10 indicates "risk 1", which is a rank in which the risk of cardiovascular disease is the lowest. This allows for the measured subject to assume that he or she is in normal health. If the resulting position is plotted in the lower right sub-region E2, the systolic blood pressure value SYS is higher than the reference value S1 and the blood vessel hardness index VSI is lower than the reference value S2. Thus, the measured subject can determine that the measurement result of the circulatory dynamics measurement apparatus 10 indicates "risk 2", which is a rank in which the risk of cardiovascular disease is the second lowest (risk is third highest). This allows for the measured subject to recognize that he or she should undergo treatment (medication etc.) to lower the blood pressure. If the resulting position is plotted in the upper left sub-region E3, the systolic blood pressure value SYS is lower than the reference value S1 and the blood vessel hardness index VSI is higher than the reference value S2. Thus, the measured subject can determine that the measurement result of the circulatory dynamics measurement apparatus 10 indicates "risk 3", which is a rank in which the risk of cardiovascular disease is the third lowest (risk is second highest). This allows for the measured subject to recognize that he or she should undergo treatment (medication etc.) to soften the blood vessel. If the resulting position is plotted in the upper right sub-region E4, the systolic blood pressure value SYS is higher than the reference value S1 and the blood vessel hardness index VSI is higher than the reference value S2. Thus, the measured subject can determine that the measurement result of the circulatory dynamics measurement apparatus 10 indicates "risk 4", which is a rank in which the risk of cardiovascular disease is the highest. This allows for the measured subject to recognize that he or she should undergo treatment (medication etc.) to lower the blood pressure value and soften the blood vessel. In this manner, under a situation in which the measured subject would have assumed that he or she is in normal health due to the conventional scheme that is based on only the blood pressure value even though there is a relatively high risk of a cardiovascular disease such as "risk 3", the circulatory dynamics measurement apparatus 10 allows for the measured subject to notice such a situation. Even when the blood pressure value is about the same, the measurement results are classified into "risk 2" and "risk 4" in accordance with the blood vessel hardness index VSI. This allows for the measured subject to recognize whether or not the blood vessel hardness is normal. If the systolic blood pressure value SYS or the blood vessel hardness index VSI is greatly separated from the reference value S1 or S2, the resulting position is plotted at a position (e.g., edge of plotting area) remote from the corresponding reference value.

As described above in detail, the first embodiment has the following advantages.

(1) The display unit 19 shows a graph, which include axes representing the systolic blood pressure value SYS and the blood vessel hardness index VSI, and a resulting position, which is defined by the systolic blood pressure value SYS and the blood vessel hardness index VSI in the plotting area of the graph. The measured subject can recognize the relationship of the systolic blood pressure value SYS and the blood vessel hardness index VSI at a glance from the resulting position defined by the systolic blood pressure value SYS and the blood vessel hardness index VSI shown in the graph. This allows the measured subject to recognize his or her condition.

(2) The display unit 19 displays the systolic blood pressure reference value S1 and the blood vessel hardness reference value S2 in the plotting area of the graph. The plotting area of the graph is divided into four sub-regions E1 to E4 by the reference values S1 and S2. The measured subject can easily assume the type and extent of the risk of cardiovascular disease from the resulting position defined by the systolic blood pressure value SYS and the blood vessel hardness index VSI. The measured subject can accurately and easily assume the extent of risk based on the distance from the resulting position, which is defined by the systolic blood pressure value SYS and the blood vessel hardness index VSI, to the reference values S1 and S2. For example, if the resulting position is shown in the sub-region E4 of risk 4, the risk is assumed to be higher as the resulting position becomes farther from the reference value S1 or S2, and the risk is estimated to be lower as the resulting position becomes closer to the reference value S1 or S2. It may be determined whether the blood pressure is high (or low) based on the distance from the resulting position to the systolic blood pressure reference value S1. In the same manner, it may be determined how hard (or soft) the blood vessel based on the distance of the resulting position from the blood vessel hardness reference value S2.

(3) The circulatory dynamics measurement apparatus 10 calculates the blood vessel hardness index VSI based on the pulse wave value acquired from the upper arm. Thus, the circulatory dynamics measurement apparatus 10 may easily be incorporated in a household sphygmomanometer. The circulatory dynamics measurement apparatus 10 acquires both of the systolic blood pressure value SYS and the blood vessel hardness index VSI. This shortens the measurement time of the systolic blood pressure value SYS and the blood vessel hardness index VSI. The display unit 19 shows the graph including the resulting position defined by the systolic blood pressure value SYS and the blood vessel hardness index VSI. The resulting position is statistically correlated with the extent of risk of cardiovascular disease such as arteriosclerosis disease. Accordingly, the resulting position in the graph allows for the measured subject to find, at an early stage, an arteriosclerosis disease, which would have been unnoticed when performing only the conventional blood pressure measurement. Thus, the circulatory dynamics measurement apparatus 10 is advantageous for preventing and treating lifestyle-related diseases.

Second Embodiment

A circulatory dynamics measurement apparatus according to a second embodiment of the present invention will now be described. In each embodiment described hereafter, same reference characters are given to those components that are the same as the corresponding components of the first embodiment. Such components will not be described in detail.

Figure 9:
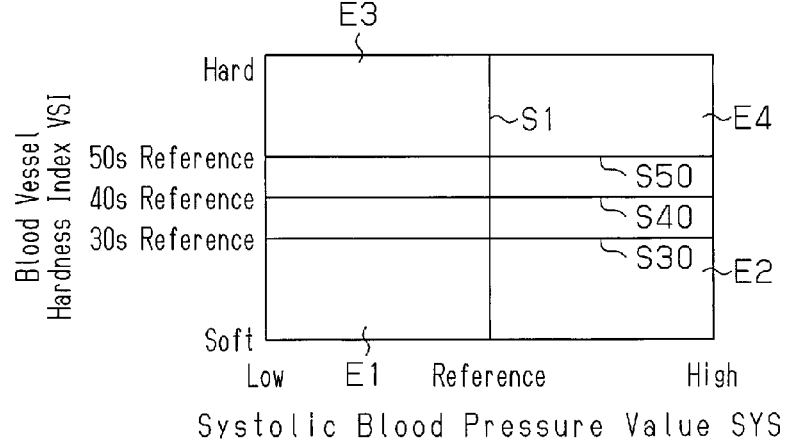
FIG. 9 is a schematic diagram of a graph shown on the display unit.

The reference value of the blood vessel hardness index VSI is known to differ depending on the age of the measured subject. Thus, the reference value of the blood vessel hardness index VSI is set in accordance with the age of the measured subject. In the example shown in FIG. 9, the display unit 19 shows a reference value S40 at the middle of the vertical axis that corresponds to a measured subject who is in the forties, a reference value S30 that corresponds to a measured subject who is in the thirties, and a reference value S50 corresponding to a measured subject who is in the fifties. The reference values S30 and S50 are shown at positions that differ from the position of the reference value S40. The measured subject can perform risk assumption based on one or more of the reference values S30, S40, S50 corresponding to his or her age and the sub-region including the resulting position shown in the graph.

As described above in detail, the second embodiment has the following advantage.

(4) The display unit 19 shows the resulting position, which is defined by the systolic blood pressure value SYS and the blood vessel hardness index VSI, and the reference values S30 to S50, which corresponding to the age of the measured subject in the graph. This allows for the measured subject to accurately estimate his or her circulatory dynamics.

Third Embodiment

A third embodiment of the present invention will now be described focusing on differences from the first embodiment.

In the third embodiment, a blood vessel hardness index VSI1 obtained by dividing the blood vessel hardness index VSI with the systolic blood pressure value SYS is used as a non-blood pressure circulatory dynamics index. The blood vessel hardness index VSI1 is obtained from equation (V1).

$$VSI1 = VSI/SYS \tag{V1}$$

Figure 10:
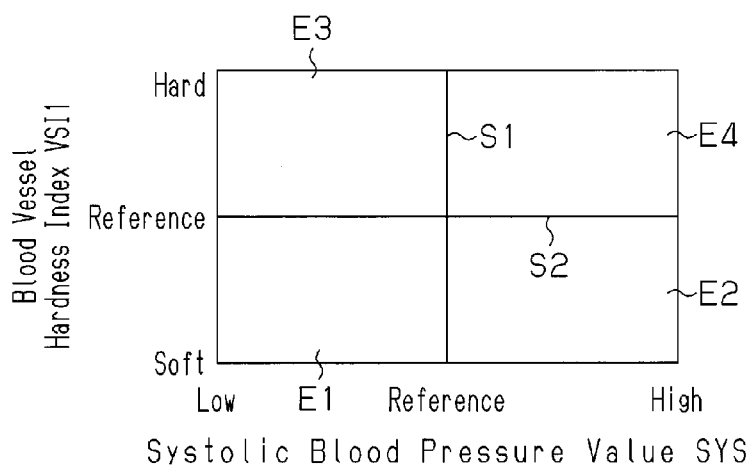
FIG. 10 is a schematic diagram of a graph shown on the display unit.

As shown in FIG. 10, the display unit 19 shows a graph including a horizontal axis representing the systolic blood pressure value SYS and a vertical axis representing the blood vessel hardness index VSI1. The reference value S2 of the blood vessel hardness index VSI1 is shown at the middle of the vertical axis.

As described above in detail, the third embodiment has the following effects.

(5) The blood vessel hardness index VSI1 calculated by dividing the blood vessel hardness index VSI with the systolic blood pressure value SYS (i.e., by correcting with the systolic blood pressure value SYS) indicates a ratio relative to the systolic blood pressure value SYS. Accordingly, the circulatory dynamics measurement apparatus 10 presents the blood vessel hardness index to the measured subject in an easily understandable manner.

Fourth Embodiment

A fourth embodiment of the present invention will now be described focusing on differences from the first embodiment.

In the fourth embodiment, a blood vessel hardness index VSI2 that takes into consideration the physical information of the measured subject is used as the non-blood pressure circulatory dynamics index. The blood vessel hardness index VSI2 is obtained from equation (V2).

$$VSI2 = A \times VSI/SYS + B \times \text{age} + C \times \text{weight} + D \times \text{height} + E \quad (V2)$$

Here, A, B, C, D, E are constants.

Figure 11:
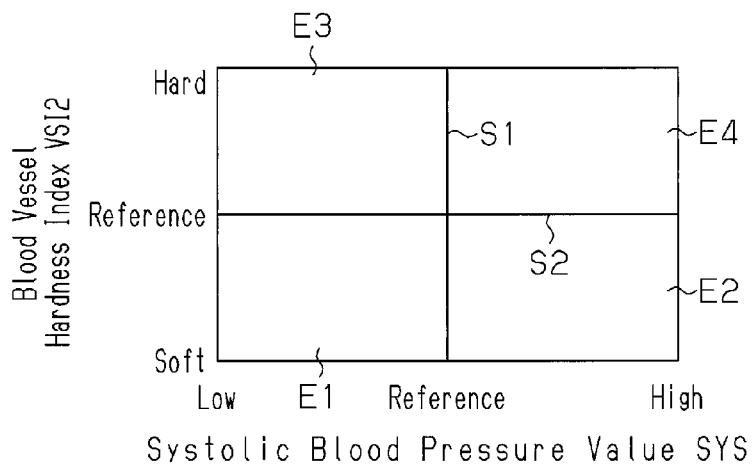
FIG. 11 is a schematic diagram of a graph shown on the display unit.

As shown in FIG. 11, the display unit 19 shows a graph including a horizontal axis representing the systolic blood pressure value SYS and a vertical axis representing the blood vessel hardness index VSI2. The reference value S2 of the blood vessel hardness index VSI2 is shown at the middle of the vertical axis.

The circulatory dynamics measurement apparatus 10 includes a nonvolatile memory (not shown) for storing the physical information of the measured subject provided through an input unit arranged in or connected to the circulatory dynamics measurement apparatus 10.

As described above in detail, the fourth embodiment has the following advantages.

(6) The blood vessel hardness index VSI2 serving as the non-blood pressure circulatory dynamics index is generated by correcting the blood vessel hardness index VSI with the systolic blood pressure value SYS and the one or plurality of physical information such as age, weight, height, and the like of the measured subject. Thus, the circulatory dynamics measurement apparatus 10 presents the measured subject with the blood vessel hardness index VSI2 that takes into consideration the physical information of the measured subject.

Fifth Embodiment

A fifth embodiment of the present invention will now be described focusing on differences from the first embodiment.

Figure 12:
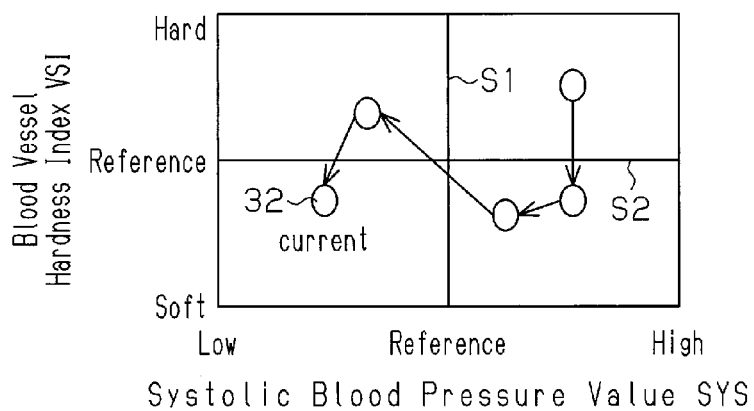
FIG. 12 is a schematic diagram of a graph shown on the display unit.

The display unit 19 of the fifth embodiment shows the most recent measurement result and the past measurement results in the graph. In the example shown in FIG. 12, measurement result marks and measurement order information are shown in the same graph. The measurement order information may be a character that indicates how many times before the measurement result was taken or may be a measurement date. As shown in FIG. 12, the measurement order information may be a figure such as an arrow shown between the marks to indicate the measurement order.

As described above in detail, the fifth embodiment has the following advantage.

(7) The display unit 19 shows marks, which indicate the most recent measurement result and the past measurement result, and the measurement order information in a graph. Therefore, the measured subject easily recognizes changes in the measurement result over time, and easily determines whether or not the measurement result has improved. When arrows indicating the measurement order are shown, the measured subject can further easily recognize the measurement order.

Sixth Embodiment

A sixth embodiment of the present invention will now be described focusing on differences from the first embodiment.

The reference value of the blood vessel hardness index VSI is known to differ in accordance with the physical information such as sex, age, weight, height, and the like of the measured subject. Thus, in the sixth embodiment, the blood vessel hardness computation unit 17 calculates the blood vessel hardness index VSI in accordance with the physical information of the measured subject.

For example, the blood vessel hardness computation unit 17 corrects the blood vessel hardness index VSI with the physical information including sex, age, weight, and height of the measured subject to calculates a blood vessel hardness index VSI3 for a male or a blood vessel hardness index VSI4 for a female. The blood vessel hardness index VSI3 for a male is obtained from equation (V3).

$$VSI3 = A1 \times VSI/SYS + B1 \times \text{age} + C1 \times \text{weight} + D1 \times \text{height} + E1 \quad (V3)$$

Here, A1, B1, C1, D1, E1 are constants.

The blood vessel hardness index VSI4 for a female is obtained from equation (V4).

$$VSI4 = A2 \times VSI/SYS + B2 \times \text{age} + C2 \times \text{weight} + D2 \times \text{height} + E2 \quad (V4)$$

Here, A2, B2, C2, D2, E2 are constants.

When the measured subject is a male (when input as male), the display unit 19 shows a graph including a horizontal axis representing the systolic blood pressure value SYS and a vertical axis representing the male blood vessel hardness index VS13. The reference value S3 of the male blood vessel hardness index VS13 is shown at the middle of the vertical axis.

When the measured subject is a female (when input as female), the display unit 19 shows a graph including a horizontal axis representing the systolic blood pressure value SYS and a vertical axis representing the female blood vessel hardness index VS14. The reference value S4 of the female blood vessel hardness index VS14 is shown at the middle of the vertical axis.

The circulatory dynamics measurement apparatus 10 includes a nonvolatile memory (not shown) for storing the physical information of the measured subject provided through the input unit arranged in or connected to the circulatory dynamics measurement apparatus 10.

As described above in detail, the sixth embodiment has the following advantage.

(8) The display unit 19 shows the blood vessel hardness indices VS13 and VS14 in which the blood vessel hardness index VSI is corrected with the systolic blood pressure value SYS and the physical information including the sex, age, weight, and height of the measured subject. Thus, the measured subject recognizes a further accurate blood vessel hardness index that takes into consideration the physical information of the measured subject.

Seventh Embodiment

A seventh embodiment of the present invention will now be described focusing on differences from the first embodiment.

In the seventh embodiment, based on a characteristic line of the cumulatively added pulse wave value ratio and predetermined first and second values (first value<second value), the blood vessel hardness computation unit 17 obtains a compression pressure P0, which corresponds to when the cumulatively added pulse wave value ratio is the first value, and a compression pressure P1, which corresponds to when the cumulatively added pulse wave value ratio is the second value. The blood vessel hardness computation unit 17 calculates the ratio (P1/P0) of the obtained compression pressures, and provides the display unit 19 with the ratio (P1/P0) as a blood vessel hardness index VSI5.

In the illustrated example, the blood vessel hardness computation unit 17 specifies the compression pressure P0 of when the cumulatively added pulse wave value ratio is 20% (first value) and the compression pressure P1 of when the calculated cumulatively added pulse wave value ratio is 80% (second value). The blood vessel hardness computation unit 17 calculates a ratio (P1/P0) of the specified compression pressures, and provides the same to the display unit 19 as the blood vessel hardness index VSI5.

The operation of the display unit 19 will now be described.

Figure 15:
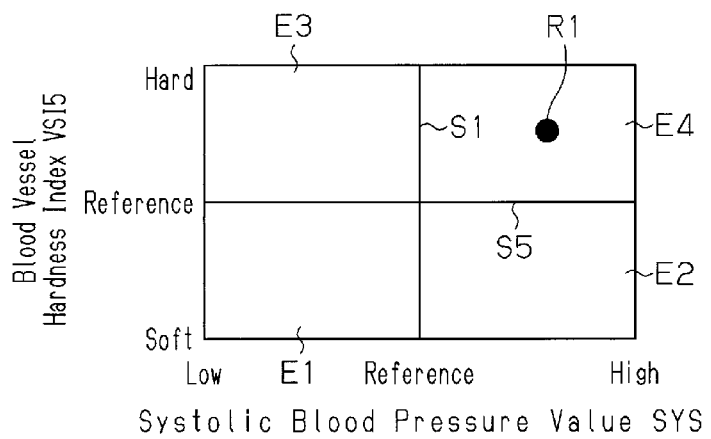
FIG. 15 is a schematic diagram of a graph shown on the display unit.

As shown in FIG. 15, the display unit 19 shows a graph including a horizontal axis representing the systolic blood pressure value SYS and a vertical axis representing the blood vessel hardness index VSI5. A reference value S5 of the blood vessel hardness index VSI5 is shown at the middle of the vertical axis. The display unit 19 shows a resulting position (mark) R1 defined by the systolic blood pressure value SYS provided from the blood pressure computation unit 18 and the blood vessel hardness index VSI5 provided from the blood vessel hardness computation unit 17.

The relationship of the characteristic line of the cumulatively added pulse wave value ratio and the blood vessel hardness index VSI5 will now be described.

Figure 16A:
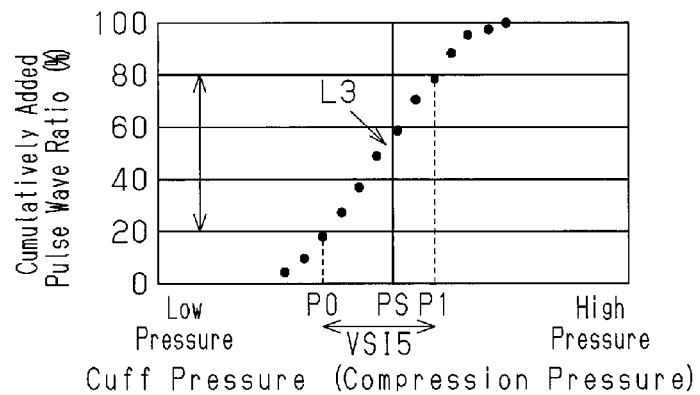
FIG. 16A and FIG. 16B are graphs showing the relationship of the cumulatively added pulse wave value ratio and the cuff pressure.
Figure 16B:
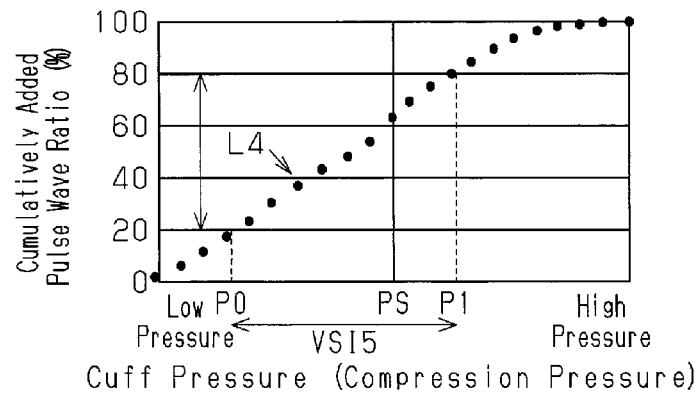

FIG. 16A shows a characteristic line L3 of the cumulatively added pulse wave value ratio generated based on the pulse wave detected from a soft blood vessel. FIG. 16B shows a characteristic line L4 of the cumulatively added pulse wave value ratio generated based on the pulse wave detected from a hard blood vessel.

When comparing the characteristic line L3 and the characteristic line L4, the ratio (P1/P0) of the compression pressure is smaller in the soft blood vessel than in the hard blood vessel. Accordingly, the ratio (P1/P0) can indicate the blood vessel hardness.

As described above in detail, the seventh embodiment has the following advantage.

(9) The blood vessel hardness computation unit 17 calculates the blood vessel hardness index VSI5 by acquiring the ratio (P1/P0) of the compression pressures. Thus, compared to when calculating the blood vessel hardness index VSL1 by dividing the blood vessel hardness index VSL with the systolic blood pressure value SYS or when calculating the blood vessel hardness index VSI2 to VSI4 that takes into consideration the physical information, the computation load of the blood vessel hardness computation unit 17 required for the calculation of the blood vessel hardness index VSI5 is small. The blood vessel hardness computation unit 17 may calculate the ratio (P1/P0) using the characteristic line L2 of the cumulatively added pulse wave value shown in FIG. 5 instead of the characteristic lines L3, L4 of the cumulatively added pulse wave value ratio.

Eighth Embodiment

An eighth embodiment of the present invention will now be described focusing on differences from the first embodiment.

In the eighth embodiment, based on the characteristic line of the cumulatively added pulse wave value ratio and predetermined first and second values (first value<second value), the blood vessel hardness computation unit 17 obtains a cumulatively added pulse wave value ratio U0 corresponding to when the compression pressure is the first value and a cumulatively added pulse wave value ratio U1 corresponding to when the compression pressure is the second value. The blood vessel hardness computation unit 17 calculates a ratio (U1/U0) of the obtained cumulatively added pulse wave value ratios, and provides the display unit 19 with the ratio (U1/U0) of the calculated cumulatively added pulse wave value ratios as a blood vessel hardness index VSI6.

In the illustrated example, the blood vessel hardness computation unit 17 obtains the cumulatively added pulse wave value ratio U0 of when the compression pressure is 80 mmHg (first value) and the cumulatively added pulse wave value ratio U1 of when the compression pressure is 120 mmHg (second value). The blood vessel hardness computation unit 17 calculates the ratio (U1/U0) of the specified cumulatively added pulse wave value ratios, and provides the display unit 19 with the ratio as the blood vessel hardness index VSI6.

The operation of the display unit 19 will now be described.

Figure 17:
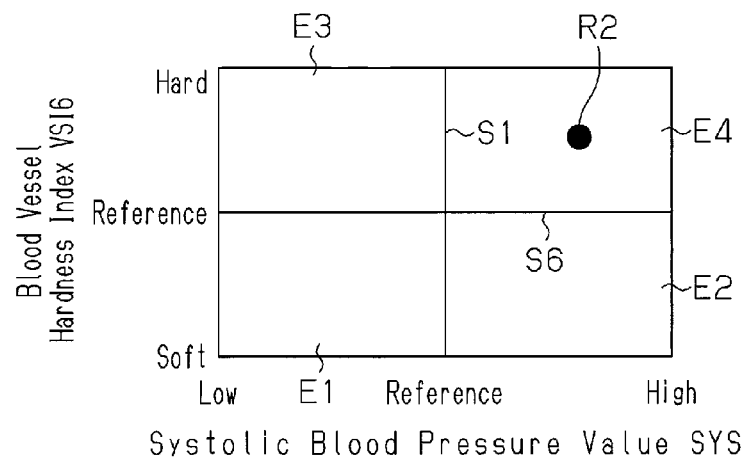
FIG. 17 is a schematic diagram of a graph shown on the display unit.

As shown in FIG. 17, the display unit 19 shows a graph including a horizontal axis representing the systolic blood pressure value SYS and a vertical axis representing the blood vessel hardness index VSI6. A reference value S6 of the blood vessel hardness index VSI6 is shown at the middle of the vertical axis. The display unit 19 shows a resulting position (mark) R2 defined by the systolic blood pressure value SYS provided from the blood pressure computation unit 18 and the blood vessel hardness index VSI6 provided from the blood vessel hardness computation unit 17.

The relationship of the characteristic line of the cumulatively added pulse wave value ratio and the blood vessel hardness index VSI6 will now be described.

Figure 18A:
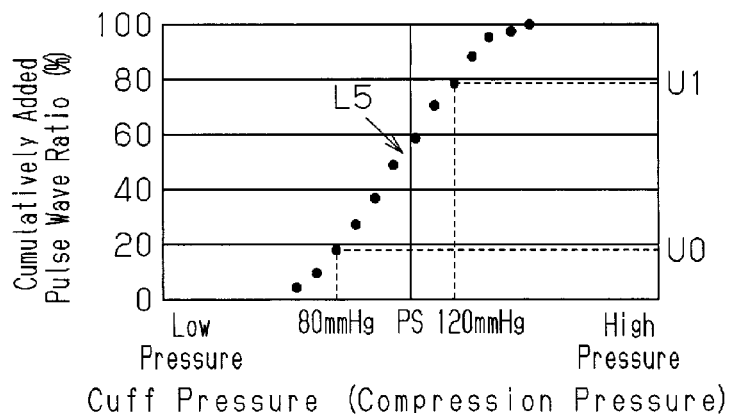
FIG. 18A and FIG. 18B are graphs showing the relationship of the cumulatively added pulse wave value ratio and the cuff pressure.
Figure 18B:
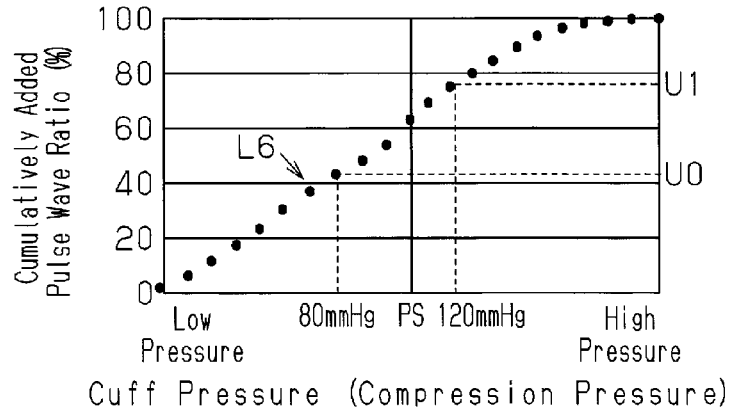

FIG. 18A shows a characteristic line L5 of the cumulatively added pulse wave value ratio generated based on the pulse wave detected from the soft blood vessel. FIG. 18B shows a characteristic line L6 of the cumulatively added pulse wave value ratio generated based on the pulse wave detected from the hard blood vessel.

When comparing the characteristic line L5 and the characteristic line L6, the ratio (U1/U0) of the cumulatively added pulse wave value ratios, that is, the blood vessel hardness index VSI6 is greater in the soft blood vessel than in the hard blood vessel. Therefore, the ratio (U1/U0) can indicate the blood vessel hardness.

As described above in detail, the eighth embodiment has the following advantage.

(10) The blood vessel hardness computation unit 17 calculates the blood vessel hardness index VSI6 by acquiring the ratio (U1/U0) of the cumulatively added pulse wave value ratio. Thus, compared to when calculating the blood vessel hardness index VSL1 by dividing the blood vessel hardness index VSL with the systolic blood pressure value SYS or when calculating the blood vessel hardness indices VSI2 to VSI4 that take into consideration the physical information, the computation load of the blood vessel hardness computation unit 17 required for the calculation of the blood vessel hardness index VSU6 is small. The blood vessel hardness computation unit 17 may calculate the ratio (U1/U0) using the characteristic line L2 of the cumulatively added pulse wave value ratio shown in FIG. 5 instead of the characteristic lines L5, L6 of the cumulatively added pulse wave value ratio.

Ninth Embodiment

A ninth embodiment of the present invention will now be described focusing on differences from the first embodiment.

The circulatory dynamics measurement apparatus 10 of the ninth embodiment includes a condition determination unit that executes a process for determining whether or not the systolic blood pressure value SYS exceeds the reference value S1 by comparing the systolic blood pressure value SYS and the reference value S1 and a process for determining whether or not the blood vessel hardness index VSI exceeds the reference value S2 by comparing the blood vessel hardness index VSI and the reference value S2. The condition determination unit is incorporated in, for example, the display unit 19, and can acquire the systolic blood pressure value SYS and the blood vessel hardness index VSI provided to the display unit 19.

The condition determination unit determines which one of the sub-regions E1 to E4 the resulting position is shown in by performing the process for determining whether or not the blood vessel hardness index VSI exceeds the reference value S2 together with the process for determining whether or not the systolic blood pressure value SYS exceeds the reference value S1 to.

For example, the condition determination unit determines that the systolic blood pressure value SYS and the blood vessel hardness index VSI exceed the reference values S1, S2, respectively. The condition determination unit determines that the systolic blood pressure value SYS exceeds the reference value S1 and the blood vessel hardness index VSI does not exceed the reference value S2. The condition determination unit determines that the systolic blood pressure value SYS does not exceed the reference value S1 and the blood vessel hardness index VSI exceeds the reference value S1. The condition determination unit determines that the systolic blood pressure value SYS does not exceed the reference value S1 and the blood vessel hardness index VSI does not exceed the reference value S2. The condition determination unit then determines (obtains) the sub-region E1 to E4 corresponding to the determination result.

More specifically, the condition determination unit determines that the resulting position is shown in the sub-region E4 when the systolic blood pressure value SYS exceeds the references value S1 and the blood vessel hardness index VSI exceeds the reference value S2. The condition determination unit determines that the resulting position is shown in the sub-region E2 when the systolic blood pressure value SYS exceeds the references value S1 and the blood vessel hardness index VSI does not exceed the reference value S2. The condition determination unit determines that the resulting position is shown in the sub-region E3 when the systolic blood pressure value SYS does not exceed the references value S1 and the blood vessel hardness index VSI exceeds the reference value S2. The condition determination unit determines that the resulting position is shown in the sub-region E1 when the systolic blood pressure value SYS does not exceed the references value S1 and the blood vessel hardness index VSI does not exceed the reference value S2.

In accordance with the determination result of the condition determination unit, the display unit 19 shows a message or an image of the content corresponding to the sub-region in which the resulting position is shown. The circulatory dynamics measurement apparatus 10 may include a non-volatile memory (not shown) for storing predetermined messages or images corresponding to the sub-regions E1 to E4.

Figure 19:
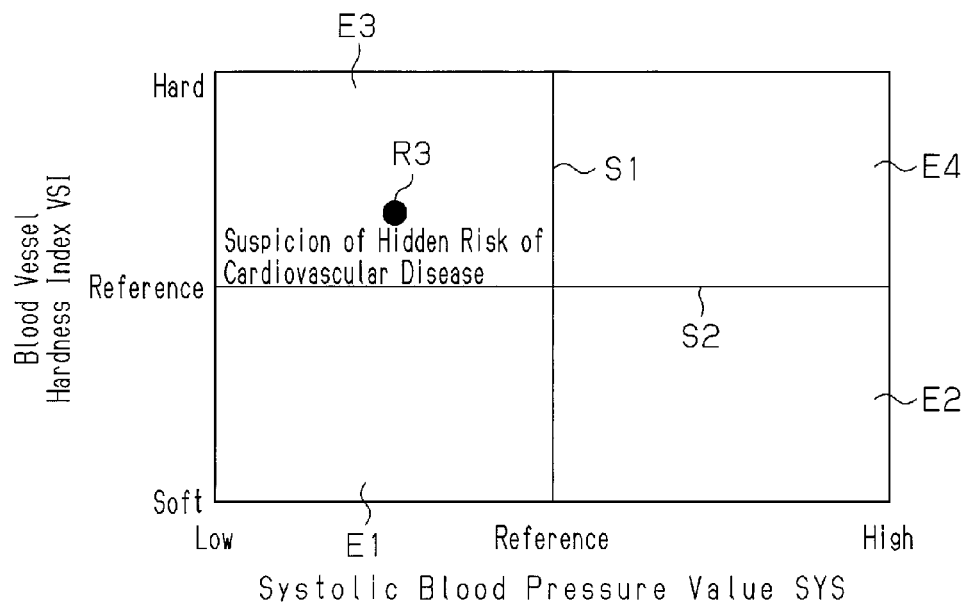
FIG. 19 is a schematic diagram of a graph shown on the display unit.

In the example of FIG. 19, the systolic blood pressure value SYS does not exceed the reference value S1 and the blood vessel hardness index VSI exceeds the reference value S2. Thus, the display unit 19 shows the resulting position (mark) R3 in the sub-region E3.

In accordance with the determination result of the condition determination unit, the display unit 19 shows a message in the sub-region E3. The text of the message corresponds to the sub-region E3, specifically, "suspicion of hidden risk of cardiovascular disease". The content of the message is an example and may be changed. The position where the message or the image is shown may be changed.

In cardiovascular diseases such as arteriosclerosis, diabetes, kidney disease, and the like, the blood vessel flexibility may start to deteriorate when the blood pressure is still normal. Accordingly, by showing the message of "suspicion of hidden risk of cardiovascular disease" on the display unit 19, the type and extent of risk of the cardiovascular disease of the measured subject can be presented so that it can be easily understood. This allows for a cardiovascular disease to be found at an earlier stage.

When the condition determination unit determines that the resulting position is shown in the sub-region E4, the display unit 19 shows a message, the content of which corresponds to the sub-region E4, specifically, "high risk".

As described above in detail, the ninth embodiment has the following advantage.

(11) The condition determination unit performs the process for determining whether or not the systolic blood pressure value SYS exceeds the reference value S1 and the process for determining whether or not the blood vessel hardness index VSI exceeds the reference value S2. As a result, the condition determination unit determines which one of the sub-regions E1 to E4 in the display unit 19 shows the resulting position. The display unit 19 shows an image of the determination result of the condition determination unit, that is, the content (text message in the ninth embodiment) corresponding to the sub-region E1 to E4 in which the resulting position is shown. In particular, when determined that the resulting position is shown in the sub-region E3, "suspension of hidden risk of cardiovascular disease" is shown. Thus, the circulatory dynamics measurement apparatus 10 presents the circulatory dynamics of the measured subject in a manner that is further easier to understand. This allows for the measured subject to find a vascular disease at an early stage.

Figure 20:
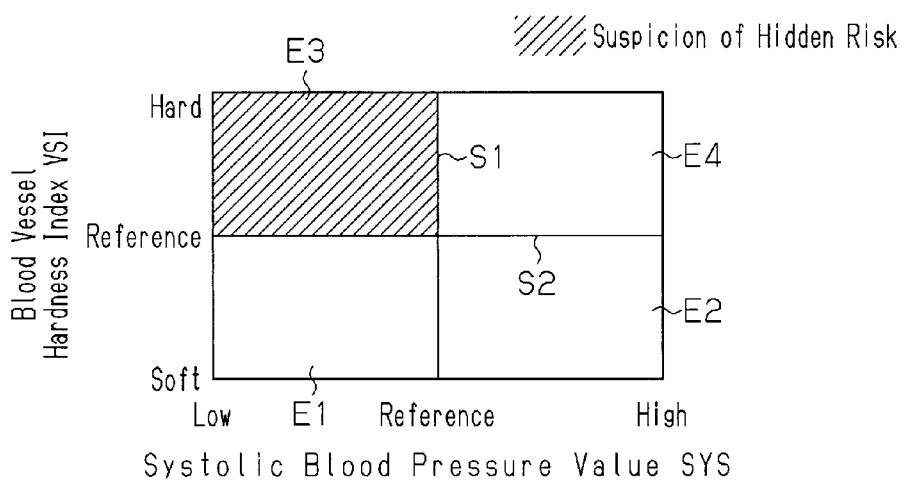
FIG. 20 is a schematic diagram of a graph shown on the display unit.

In the ninth embodiment, the display unit 19 shows the message or the image for notifying the measured subject of the "suspicion of hidden risk of the cardiovascular disease". In the example shown in FIG. 20, instead of showing the message or image, the display unit 19 patterns the sub-region E3 to indicate that this region is where there is the "suspicion of hidden risk of cardiovascular disease". The pattern may be shading, hatching, a different color, and the like. In this case, the measured subject can visually recognize the "suspicion of hidden risk of cardiovascular disease" by looking at the resulting position shown in the sub-region E3. In this case, the circulatory dynamics measurement apparatus 10 does not have to include the condition determination unit.

Tenth Embodiment

A tenth embodiment of the present invention will now be described focusing on differences from the first embodiment.

Figure 21:
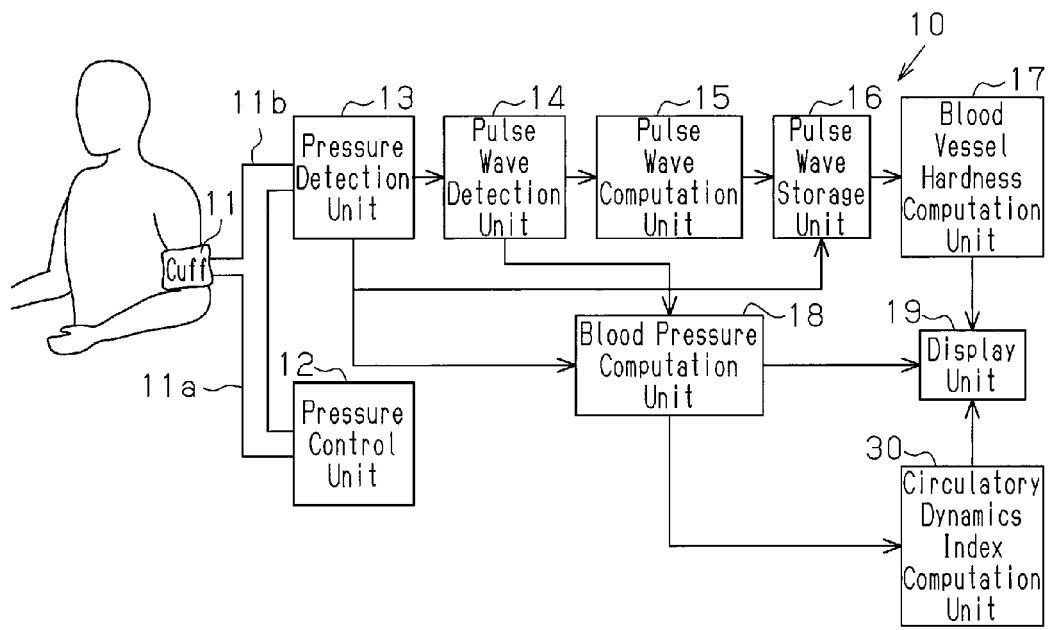
FIG. 21 is a block diagram of a circulatory function measurement apparatus according to a tenth embodiment.

The circulatory dynamics measurement apparatus 10 of the tenth embodiment shown in FIG. 21 includes a blood pressure computation unit 18 that calculates the blood pressure as a first circulatory dynamics index, a blood vessel hardness computation unit 17 that calculates a blood vessel hardness index serving as a second circulatory dynamics index, and a circulatory dynamics index computation unit 30 that calculates a third circulatory dynamics index, which differs from the blood pressure and the blood vessel hardness. The blood pressure computation unit 18, the blood vessel hardness computation unit 17, and the circulatory dynamics index computation unit 30 are included in a calculation unit.

The well-known Framingham score, for example, is used as the third circulatory dynamics index. The Framingham score is an index that is calculated using the factors of age, sex, total cholesterol in blood, HDL cholesterol, systolic blood pressure, smoker or non-smoker, suffering from diabetes. The index indicates the probability for the occurrence of a coronary artery disease within ten years. For example, if the Framingham score is 10, the probability for the occurrence of a coronary artery disease within ten years is estimated to be 11%. If the Framingham score is 15, the probability for the occurrence of a coronary artery disease within 10 years is estimated to be 24%.

In the tenth embodiment, an input unit included in or connected to the circulatory dynamics measurement apparatus 10 is used to input test values (total cholesterol etc.) obtained through tests conducted in advance, age, and sex to the circulatory dynamics index computation unit 30. The circulatory dynamics index computation unit 30 is connected to the blood pressure computation unit 18, and the systolic blood pressure value SYS is provided from the blood pressure computation unit 18. Based on the input test values, age, sex, and systolic blood pressure value SYS, the circulatory dynamics index computation unit 30 executes a calculation program, which is stored in advance, to calculate the Framingham score. The circulatory dynamics index computation unit 30 provides the display unit 19 with the calculated Framingham score.

The display unit 19 shows a mark at the resulting position obtained from the systolic blood pressure value SYS and the blood vessel hardness index VSI. The mark is shown in a display mode (shape, color, flashing, pattern, etc.) corresponding to the Framingham score.

Figure 22:
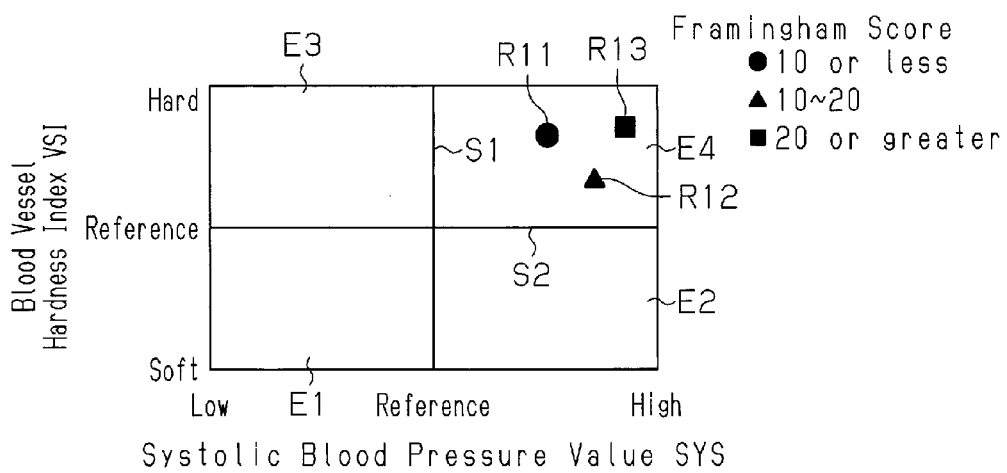
FIG. 22 is a schematic diagram of a graph shown on the display unit.

The display mode of the mark will now be described with reference to FIG. 22.

For example, when the Framingham score is less than or equal to 10, the display unit 19 shows a mark R11 having the shape of a solid circle. When the Framingham score is between 10 and 20, the display unit 19 shows a mark R12 having the shape of a solid triangle. When the Framingham score is greater than or equal 20, the display unit 19 displays a mark R13 having the shape of a solid square. In FIG. 22, the marks are separated from one another so that the shapes of the marks R11 to R13 can be easily understood.

As described above in detail, the tenth embodiment has the following advantage.

(12) The display unit 19 shows a mark in a display mode corresponding to the Framingham score (third circulatory dynamics index) at the resulting position obtained from the systolic blood pressure value SYS and the blood vessel hardness index VSI. Thus, even if the resulting position is shown in the same sub-region, the display mode of the mark may be changed by the third circulatory dynamics index. The measured subject can easily recognize, from the display mode of the mark, the difference in the extent of the third circulatory dynamics index. For example, if the resulting position is shown in the sub-region E4, the measured subject can assume, in detail, the extent of a risk of a disease based on the display mode of the mark.

Even if the resulting position is in the sub-region E3 showing that there is a high hidden risk of a cardiovascular disease, the measured subject can easily assume that the blood vessel is hard due to age if the Framingham score is less than or equal to 10. That is, the circulatory dynamics measurement apparatus 10 notifies the measured subject the circulatory dynamics in further detail. By changing the display mode of the mark, more information on the circulatory dynamics can be shown. This allows for the measured subject to recognize the condition of the circulatory dynamics at a glance.

The embodiments described above may be modified as described below.

Figure 13:
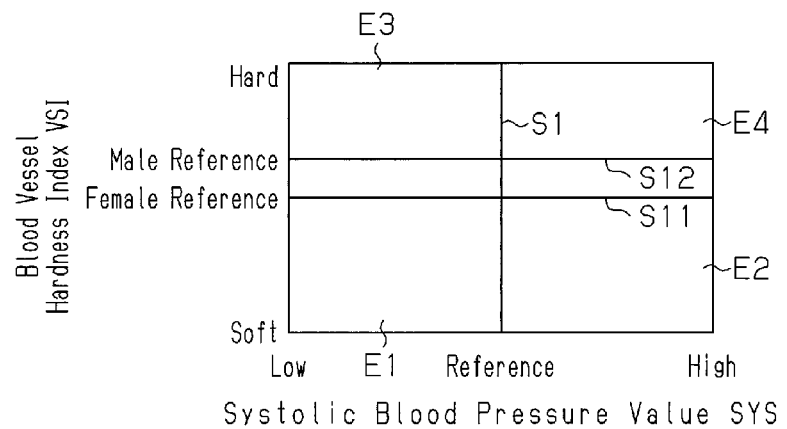
FIG. 13 is a schematic diagram of a graph shown on the display unit.

In the second embodiment, the display unit 19 shows the reference value S2 of the blood vessel hardness index VSI in correspondence with age but may show the reference value S2 of the blood vessel hardness index VSI in correspondence with physical information other than age. For example, it is known that the reference value S2 differs between male and female. Thus, the display unit 19 may show the reference values S11 and S12 in correspondence with sex, as shown in FIG. 13. The display unit 19 may also show the reference value S2 in correspondence with physical information such as weight. The display unit 19 may show the reference value S1 of the systolic blood pressure value SYS in correspondence with the physical information.

In the second embodiment, the display unit 19 shows the reference values for a plurality of blood vessel hardness indices VSI. However, the display unit 19 may show only the reference value corresponding to the input physical information (age etc.) of the measured subject. This allows for the measured subject to easily recognize the region including the resulting position.

Figure 14A:
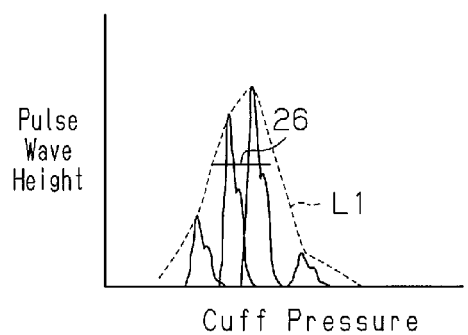
FIG. 14A and FIG. 14B are graphs showing the relationship of the cuff pressure and the amplitude value of the detected pulse wave.
Figure 14B:
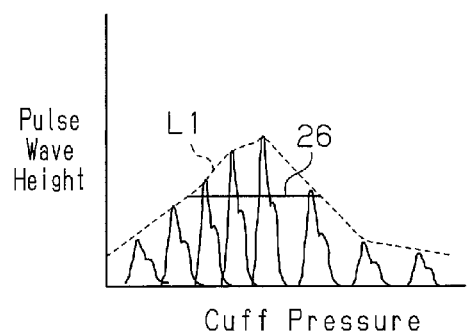

In the embodiments described above, the blood vessel hardness index VSI is calculated using the cumulatively added pulse wave value ratio, in which the cumulatively added pulse wave value generated by cumulatively adding the amplitude values of all of the pulse waves obtained during the blood pressure measurement is standardized as 100%. However, the blood vessel hardness index VSI may be calculated from the envelope L1 indicating the relationship of the amplitude value of the pulse wave and the present compression pressure. For example, as shown in FIG. 14, the pressure width 26 at the position lower by a predetermined ratio from the vertex of the envelope L1 may be set as the blood vessel hardness index VSI. The envelope L1 of when the blood vessel is soft is shown in FIG. 14A, and the envelope L1 of when the blood vessel is hard is shown in FIG. 14B.

In the third embodiment, the systolic blood pressure value SYS is used to correct the blood vessel hardness index VSI. However, the diastolic blood pressure value DIA or the average blood pressure value MEAN may be used in the same manner to correct the blood vessel hardness index VSI.

In the embodiments described above, the display unit 19 shows the graph, which includes the axes representing the systolic blood pressure value SYS and the blood vessel hardness index VSI, and the resulting position in the graph. In a further example, the display unit 19 may display a graph, which includes the axes representing the diastolic blood pressure value DIA and the blood vessel hardness index VSI, and the resulting position in the graph. In another example, the display unit 19 may display a graph, which includes axes representing the average blood pressure value MEAN and the blood vessel hardness index VSI, and the resulting position in the graph.

In the fourth embodiment, BMI (weight/height$^2$) that combines weight and height may be used in equation (V2).

In the embodiments described above, the display unit 19 displays the resulting position, which is defined by the calculated systolic blood pressure value SYS and the calculated blood vessel hardness index VSI, with a mark so that the measured subject can determine what kind of a risk exist. In another example, the circulatory dynamics measurement apparatus 10 includes a determination unit that determines what kind of a risk exists based on the calculated systolic blood pressure value SYS and the calculated blood vessel hardness index VSI. For example, the calculated systolic blood pressure value SYS and the blood vessel hardness index VSI are input to the determination unit. The determination unit compares the reference value S1 and the calculated systolic blood pressure value SYS and determines whether or not the reference value S1 has been exceeded. The determination unit also compares the reference value S2 and the calculated blood vessel hardness index VSI to determine whether or not the reference value S2 has been exceeded. The determination unit sets risk 1 when determining that the systolic blood pressure value SYS and the blood vessel hardness index VSI both do not exceed the reference values S1 and S2. The determination unit sets risk 2 when determining that the systolic blood pressure value SYS exceeds the reference value S1 but the blood vessel hardness index VSI does not exceed the reference value S2. The determination unit sets risk 3 when determining that the systolic blood pressure value SYS does not exceed the reference value S1 but the blood vessel hardness index VSI exceeds the reference value S2. The determination unit sets risk 1 when determining that the systolic blood pressure value SYS does not exceed the reference value S1 and the blood vessel hardness index VSI does not exceed the reference value S2. The display unit 19 shows a message, image, or pattern indicating the determination result of the determination unit. This allows for the measured subject to easily determine what kind of risk there is. In this case, the mark indicating the resulting position may not be shown in the plotting area of the graph.

In the fifth embodiment, an arrow indicating the measurement order is shown but does not have to be shown.

In the tenth embodiment, the display mode may be changed for each display region in the graph. For example, the display mode of the sub-region E3 may differ from the other sub-regions E1, E2, and E4.

Figure 23:
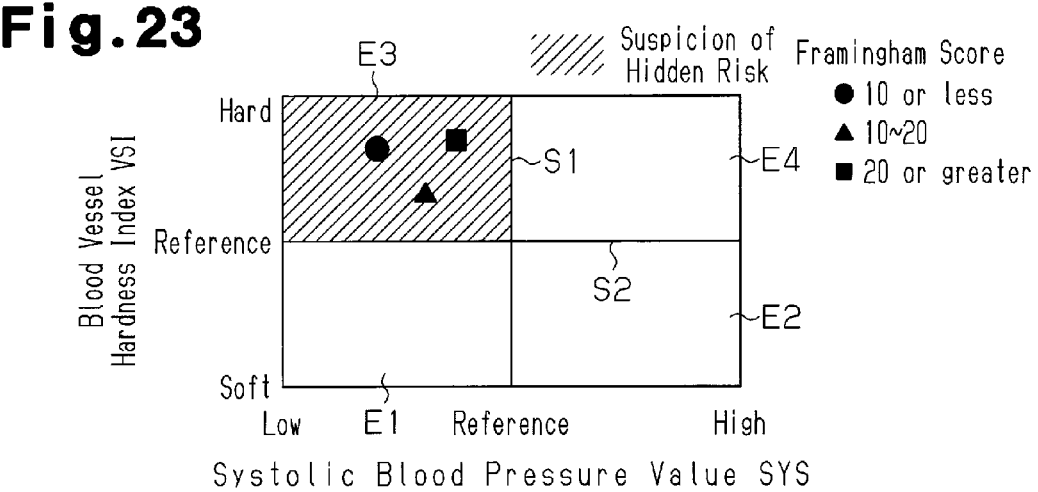
FIG. 23 is a schematic diagram of a graph shown on the display unit.

In the example of FIG. 23, the sub-region E3 is shaded, which indicates "suspicion of hidden risk of cardiovascular disease". In this configuration, the "suspicion of hidden risk of cardiovascular disease" is automatically shown when the resulting position is in the sub-region E3.

In the tenth embodiment, an index other than the Framingham score may be used as the third circulatory dynamics index. For example, eGFR (estimated glomerular filtration amount) may be used as the third circulatory dynamics index. Here, eGFR is calculated by inputting the serum creatine in the blood, age, and sex. Here, eGFR is an index representing chronic kidney disease, in which a normal value is assumed to be greater than or equal to 60 ml/min/ 1.73 m$^2$.

The circulatory dynamics index computation unit 30 calculates the eGFR based on a test value (serum creatine in the blood) obtained through a test conducted in advance, the age, and the sex, which are provided to the circulatory dynamics index computation unit 30. Then, the circulatory dynamics index computation unit 30 provides the calculation result to the display unit 19.

Figure 24:
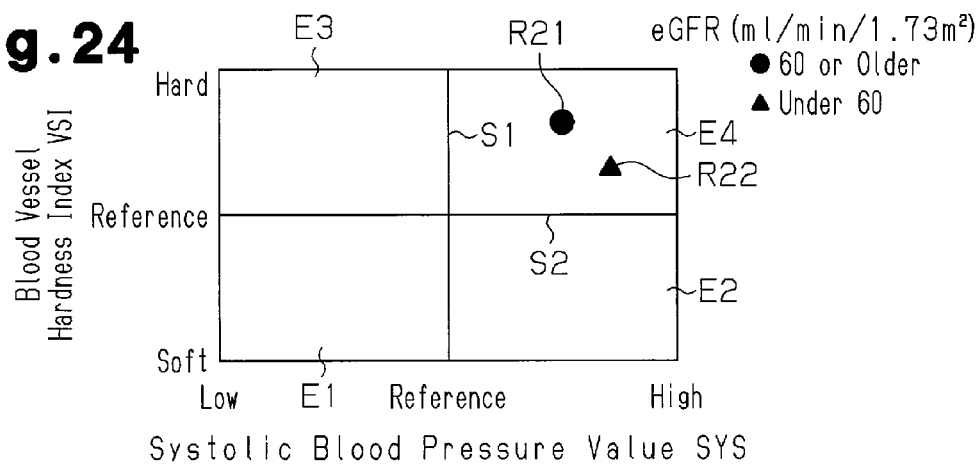
FIG. 24 is a schematic diagram of a graph shown on the display unit.

In the example shown in FIG. 24, the display unit 19 displays a resulting position mark R21 having the shape of a solid circle at the resulting position defined by the systolic blood pressure value SYS and the blood vessel hardness index VSI when the eGFR is greater than or equal to 60 (e.g., 80). The display unit 19 displays a resulting position mark R22 having the shape of a triangle at the resulting position defined by the systolic blood pressure value SYS and the blood vessel hardness index VSI when the eGFR is smaller than 60 (e.g., 50). Thus, even if the resulting positions are both within the same sub-region E4, the display mode of the mark is changed in accordance with the third circulatory dynamics index. The measured subject can estimate, in detail, the extent of risk of the disease based on the display mode of the mark.

An intima-media thickness IMT of the carotid artery may be used as the third circulatory dynamics index. The intima-media thickness IMT of the carotid artery can be measured with an ultrasonic tomography device.

The circulatory dynamics index computation unit 30 acquires the intima-media thickness IMT of the carotid artery measured in advance through the input unit. The intima-media thickness IMT is a standard index of an early arteriosclerosis diagnosis, and a guideline defines a thickness of greater than or equal to 1.1 mm to be a plaque.

Figure 25:
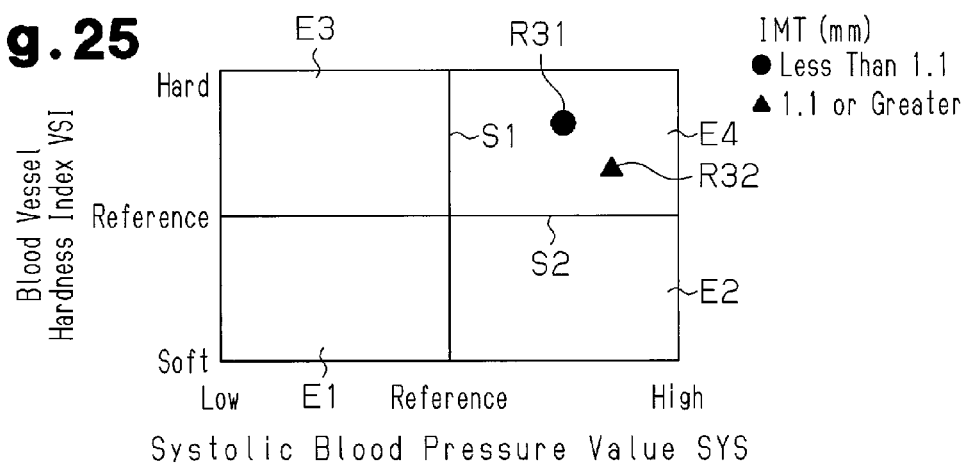
FIG. 25 is a schematic diagram of a graph shown on the display unit.

The display unit 19 shows a mark in the display mode corresponding to the intima-media thickness IMT at the resulting position obtained with the systolic blood pressure value SYS and the blood vessel hardness index VSI. In the example of FIG. 25, the display unit 19 displays a resulting position mark R31 having the shape of a solid circle at the resulting position when the intima-media thickness IMT is smaller than 1.1 mm (e.g., 0.6 mm). The display unit 19 displays a resulting position mark R32 having the shape of a solid triangle at the resulting position when the intima-media thickness IMT is greater than or equal to 1.1 mm (e.g., 2.0 mm). Thus, even if the resulting positions are both within the same display region, the measured subject can estimate, in more detail, the extent of the risk of disease based on the display mode of the mark.

In the tenth embodiment, the Framingham score, the eGFR, and the intima-media thickness IMT of the carotid artery may be simultaneously used as the third circulatory dynamics index. For example, when indicating the Framingham score in three stages, the eGFR in two stages, and the IMT in two stages, the display unit 19 prepares 12 types of marks. For example, a mark having the shape of a hollow circle is shown when the Framingham score is less than or equal to 10, the eGFR is greater than or equal to 60, and the IMT is less than 1.1. A mark having the shape of a hollow triangle is shown when the Framingham score is between 10 and 20, the eGFR is greater than or equal to 60, and the IMT is less than 1.1. A mark having the shape of a hollow square is shown when the Framingham score is greater than or equal to 20, the eGFR is greater than or equal to 60, and the IMT is less than 1.1. A mark having the shape of a solid circuit is shown when the Framingham score is less than or equal to 10, the eGFR is less than 60, and the IMT is less than 1.1. A mark having the shape of a solid triangle is shown when the Framingham score is between 10 and 20, the eGFR is less than 60, and the IMT is less than 1.1. A mark having the shape of a solid square is shown when the Framingham score is greater than or equal to 20, the eGFR is less than 60, and the IMT is less than 1.1. A mark having the shape of a hollow diamond is shown when the Framingham score is less than or equal to 10, the eGFR is greater than or equal to 60, and the IMT is greater than or equal to 1.1. A mark having the shape of a hollow reversed triangle is shown when the Framingham score is between 10 and 20, the eGFR is greater than or equal to 60, and the IMT is greater than or equal to 1.1. A mark having the shape of a hollow star is shown when the Framingham score is greater than or equal to 20, the eGFR is greater than or equal to 60, and the IMT is greater than or equal to 1.1. A mark having the shape of a solid diamond is shown when the Framingham score is less than or equal to 10, the eGFR is less than 60, and the IMT is greater than or equal to 1.1. A mark having the shape of a solid reversed triangle shape is shown when the Framingham score is between 10 and 20, the eGFR is less than 60, and the IMT is greater than or equal to 1.1. A mark having the shape of a solid star is shown when the Framingham score is greater than or equal to 20, the eGFR is less than 60, and the IMT is greater than or equal to 1.1.

In the embodiments described above, the blood vessel hardness index VSI may be changed to that obtained from one of equations X1 to X30. Here, P0 shown below is the compression pressure corresponding to when the calculated cumulatively added pulse wave value ratio is a predetermined first value in the characteristic line. P1 is the compression pressure corresponding to when the calculated cumulatively added pulse wave value ratio is a predetermined second value (where, first value<second value). U0 is the cumulatively added pulse wave value ratio corresponded when the compression pressure is a predetermined third value. U1 is the cumulatively added pulse wave value ratio corresponding to when the compression pressure is a predetermined fourth value (where, third value<fourth value). Here, log is the logarithmic function. Further, In is the function that returns the base—constant e logarithm (natural logarithm).

$$VSI = P0/P1 \quad \text{(equation X1)}$$

$$VSI = U0/U1 \quad \text{(equation X2)}$$

$$VSI = (P1/P0)/(U1/U0) \quad \text{(equation X3)}$$

$$VSI = (P0/P1)/(U0/U1) \quad \text{(equation X4)}$$

$$VSI = (U1/U0)/(P1/P0) \quad \text{(equation X5)}$$

$$VSI = (U0/U1)/(P0/P1) \quad \text{(equation X6)}$$

$$VSI = \log(P1/P0) \quad \text{(equation X7)}$$

$$VSI = \ln(P1/P0) \quad \text{(equation X8)}$$

$$VSI = (P1/P0)^2 \quad \text{(equation X9)}$$

$$VSI = \log(P0/P1) \quad \text{(equation X10)}$$

$$VSI = \ln(P0/P1) \quad \text{(equation X11)}$$

$$VSI = (P0/P1)^2 \quad \text{(equation X12)}$$

$$VSI = \log(U1/U0) \quad \text{(equation X13)}$$

$$VSI = \ln(U1/U0) \quad \text{(equation X14)}$$

$$VSI = (U1/U0)^2 \quad \text{(equation X15)}$$

$$VSI = \log(U0/U1) \quad \text{(equation X16)}$$

$$VSI = \ln(U0/U1) \quad \text{(equation X17)}$$

$$VSI = (U0/U1)^2 \quad \text{(equation X18)}$$

$$VSI = \log\{(P1/P0)/(U1/U0)\} \quad \text{(equation X19)}$$

$$VSI = \ln\{(P1/P0)/(U1/U0)\} \quad \text{(equation X20)}$$

$$VSI = \{(P1/P0)/(U1/U0)\}^2 \quad \text{(equation X21)}$$

$$VSI = \log\{(P0/P1)/(U0/U1)\} \quad \text{(equation X22)}$$

$$VSI = \ln\{(P0/P1)/(U0/U1)\} \quad \text{(equation X23)}$$

$$VSI = \{(P0/P1)/(U0/U1)\}^2 \quad \text{(equation X24)}$$

$$VSI = \log\{(U1/U0)/(P1/P0)\} \quad \text{(equation X25)}$$

$$VSI = \ln\{(U1/U0)/(P1/P0)\} \quad \text{(equation X26)}$$

$$VSI = \{(U1/U0)/(P1/P0)\}^2 \quad \text{(equation X27)}$$

$$VSI = \log\{(U0/U1)/(P0/P1)\} \quad \text{(equation X28)}$$

$$VSI = \ln\{(U0/U1)/(P0/P1)\} \quad \text{(equation X29)}$$

$$VSI = \{(U0/U1)/(P0/P1)\}^2 \quad \text{(equation X30)}$$

In the embodiments described above, the cumulatively added pulse wave value ratio is used to calculate the blood vessel hardness index VSI. However, the cumulatively added pulse wave value may be used in lieu of the cumulatively added pulse wave value ratio to calculate the blood vessel hardness index VSI.

The cumulatively added pulse wave value is generated by cumulatively adding the pulse wave values (amplitude value X of the pulse wave W1) in the order of the corresponding compression pressures, as described above. In other words, the amplitude value of the measured pulse wave W1 is sequentially added when the compression pressure changes, and the cumulatively added pulse wave value is calculated in correspondence with the compression pressure. The obtained cumulatively added pulse wave values are plotted in the order of the corresponding compression pressures to obtain the characteristic line.

The blood vessel hardness computation unit 17 calculates the blood vessel hardness index VSI based on the ratio of the cumulatively added pulse wave value corresponding to the predetermined first compression pressure and cumulatively added pulse wave value corresponding to the second compression pressure, which differs from the first compression pressure value, in the characteristic line.

The blood vessel hardness computation unit 17 can calculate the blood vessel hardness index VSI based on the ratio of the compression pressure corresponding to the predetermined first cumulatively added pulse wave value and the compression pressure corresponding to the second cumulatively added pulse wave value, which differs from the first cumulatively added pulse wave value, in the characteristic line.

In the seventh embodiment, the compression pressure value corresponding to when the cumulatively added pulse wave value ratio is 20% (first value) is represented by P0, and the compression pressure value corresponding to when the cumulatively added pulse wave value ratio is 80% (second value) is represented by P1. As long as the first value and the second value differ from each other, the first value and the second value may be changed to acquire P0 and P1. For example, the first value may be 10%, and the second value may be 90%.

In the eighth embodiment, the cumulatively added pulse wave value ratio of when the compression pressure is 80 mmHg (first value) is represented by U0, and the cumulatively added pulse wave value ratio of when the compression pressure is 120 mmHg (second value) is represented by U1 with reference to the characteristic line. As long as the first value and the second value differ from each other, the first value and the second value may be changed to acquire U0 and U1. For example, the first value may be 70 mmHg, and the second value may be 100 mmHg.

Technical concepts that can be understood from the above described embodiments and modifications are listed below.

(i) The circulatory dynamics measurement apparatus according to any one of claims 6 to 8, characterized in that the blood vessel hardness information is calculated through a computing equation that sets one or more pieces of physical information as variables, multiplies the variables by a weighting coefficient of the measured subject, and adds all of the multiplied values.

(ii) The circulatory dynamics measurement apparatus according to any one of claims 6 to 8, characterized in that the calculation unit calculates the blood vessel hardness index in accordance with a computing equation that includes a coefficient corresponding to sex.

(iii) The circulatory dynamics measurement apparatus according to any one of claims 1 to 12, being characterized by a condition determination unit that determines whether or not the calculated blood pressure exceeds a blood pressure reference value and determines whether or not the calculated non-blood pressure circulatory dynamics index exceeds a non-blood pressure circulatory dynamics index reference value to determine the circulatory dynamics, wherein when the condition determination means determines that the calculated blood pressure does not exceed the blood pressure reference value and the calculated non-blood pressure circulatory dynamics index exceeds the non-blood pressure circulatory dynamics index reference value, the display unit shows a dedicated message, image, or pattern in accordance with the determination result.

The invention claimed is:

1. A circulatory dynamics measurement apparatus comprising:
    a cuff that compresses a predetermined region of a body of a measured subject;
    a pressure sensor that detects a compression pressure of the cuff;
    a pressure control unit that includes a pressurization pump and a discharge valve to change the compression pressure of the cuff;
    a memory that stores a pulse wave value, which is related to a magnitude of a pulse wave generated at the predetermined region based on the compression pressure, and a compression pressure, which is detected by the pressure sensor, in association with each other as the pressure control unit changes the compression pressure;
    a processor that calculates a non-blood pressure circulatory dynamics index and at least either one of a systolic blood pressure and a diastolic blood pressure and using the compression pressure and the pulse wave value that are associated with each other; and
    a display unit that shows a graph including an axis indicating blood pressure and an axis indicating a non-blood pressure circulatory dynamics index, wherein the display unit shows in a plotting area of the graph a position defined by the calculated blood pressure and the calculated non-blood pressure circulatory dynamics index, wherein the non-blood pressure circulatory dynamics index includes at least a blood vessel hardness index, and
    wherein the processor is programmed to:
        calculate a cumulatively added pulse wave value for each compression pressure by cumulatively adding the pulse wave values acquired continuously or intermittently acquired as the compression pressure changes in a detection order of the corresponding compression pressures,
        divide each cumulatively added pulse wave value by a total cumulatively added pulse wave value obtain a characteristic line generated by plotting the cumulatively added pulse wave value ratio in the detection order of the corresponding compression pressure,
        obtain a characteristic line generated by plotting the cumulatively added pulse wave value ratio in the detection order of the corresponding compression pressure,
        calculate the blood vessel hardness index based on at least one of:
            a ratio of the cumulatively added pulse wave value ratio corresponding to a predetermined first compression pressure in the characteristic line and the cumulatively added pulse wave value ratio corresponding to a second compression pressure that differs from the first compression pressure in the characteristic line, or
            a ratio of a compression pressure corresponding to a predetermined first cumulatively added pulse wave value ratio in the characteristic line and a compression pressure corresponding to a predetermined second cumulatively added pulse wave value ratio in the characteristic line,
        visually display in the plotting area of the graph of the display unit the position defined by the calculated blood pressure and the calculated blood vessel hardness index, and
        when the position defined by the calculated blood pressure and the calculated blood vessel hardness index is in a certain region in the graph, display on the display unit a message, an image, or a graphical pattern for notifying of a suspicion of hidden risk of cardiovascular disease.

2. The circulatory dynamics measurement apparatus according to claim 1, wherein the display unit shows a blood pressure reference value and a non-blood pressure circulatory dynamics index reference in the graph to divide a plotting area of the graph into a plurality of sub-regions.

3. The circulatory dynamics measurement apparatus according to claim 2, wherein the blood pressure reference value and the non-blood pressure circulatory dynamics index reference value are set in accordance with physical information of the measured subject.

4. The circulatory dynamics measurement apparatus according to claim 1, wherein the display unit shows a most recent measurement result and a past measurement result in the graph.

5. The circulatory dynamics measurement apparatus according to claim 1, wherein the processor calculates the blood vessel hardness index based on an envelope formed by a cumulatively added pulse wave value generated by cumulatively adding the pulse wave values and the compression pressure associated with the pulse wave value.

6. The circulatory dynamics measurement apparatus according to claim 1, wherein the blood vessel hardness index is a value corrected by a blood pressure.

7. The circulatory dynamics measurement apparatus according to claim 1, wherein the processor calculates a cumulatively added pulse wave value for each compression pressure by cumulatively adding the pulse wave values acquired continuously or intermittently acquired as the compression pressure changes in a detection order of the corresponding compression pressures, obtains a further characteristic line generated by plotting the cumulatively added pulse wave values in the detection order of the corresponding compression pressures, and calculates the blood vessel hardness index based on at least one of:

a ratio of a cumulatively added pulse wave value corresponding to a predetermined first compression pressure in the further characteristic line and a cumulatively added pulse wave value corresponding to a second compression pressure that differs from the first compression pressure value in the further characteristic line, or a ratio of a compression pressure corresponding to a predetermined first cumulatively added pulse wave value in the further characteristic line and a compression pressure corresponding to a second cumulatively added pulse wave value that differs from the first cumulatively added pulse wave value in the further characteristic line.

8. The circulatory dynamics measurement apparatus according to claim 1, wherein the blood vessel hardness index is corrected in accordance with physical information of a measured subject.

9. The circulatory dynamics measurement apparatus according to claim 1, wherein the blood vessel hardness index is corrected in accordance with sex.

10. The circulatory dynamics measurement apparatus according to claim 1, wherein the processor determines whether or not the calculated blood pressure exceeds a blood pressure reference value and determines whether or not the calculated non-blood pressure circulatory dynamics index exceeds the non-blood pressure circulatory dynamics index reference value to generate a determination result of the circulatory dynamics, wherein the display unit shows the message or the image corresponding to the determination result of the processor for notifying of the suspicion of hidden risk of cardiovascular disease.

11. The circulatory dynamics measurement apparatus according to claim 1, wherein the processor calculates the blood pressure as a first circulatory dynamics index, the non-blood pressure circulatory dynamics index as a second circulatory dynamics index, and a third circulatory dynamics index that differs from the first and second circulatory dynamics indices;

the display unit shows a mark at a position defined by the blood pressure and the non-blood pressure circulatory dynamics index in a plotting area of the graph; and the display unit changes a display mode of the mark in accordance with a value of the third circulatory dynamics index.

12. The circulatory dynamics measurement apparatus according to claim 11, wherein the third circulatory dynamics index is at least one selected from a Framingham score, an eGFR, or an intima-media thickness of a carotid artery.

13. A circulatory dynamics measurement apparatus comprising:

one or more processors; and a memory coupled to the one or more processors and having stored thereon computer-readable instructions that, when executed by the one or more processors, cause the circulatory dynamics measurement apparatus to perform a method of measuring circulatory dynamics of a measured subject, the method including:

changing a compression pressure of a cuff which is configured to be attached to a predetermined region of a body of a measured subject;

detecting pulse waves while changing the compression pressure of the cuff;

storing the compression pressure of the cuff whenever the pulse wave is detected;

generating a plurality of first datasets, each of the first datasets being a pair of a pulse wave value of the pulse wave, which is an amplitude of the pulse wave, and the corresponding compression pressure stored;

estimating a systolic blood pressure at least partially based on the plurality of first datasets;

calculating a cumulatively added pulse wave value for each compression pressure by cumulatively adding the pulse wave values acquired continuously or intermittently acquired when changing the compression pressure, in a detection order of the corresponding compression pressures;

dividing each cumulatively added pulse wave value by a total cumulatively added pulse wave value generated by cumulatively adding all of the pulse wave values acquired during a blood pressure measurement to calculate a cumulatively added pulse wave value ratio for each compression pressure;

generating a plurality of second datasets, each of the second datasets being a pair of the cumulatively added pulse wave value ratio and the corresponding compression pressure stored;

obtaining from the plurality of second datasets a characteristic line generated by plotting the cumulatively added pulse wave value ratios in the detection order of the corresponding compression pressures;

calculating a blood vessel hardness index based on at least one of:

a ratio of the cumulatively added pulse wave value ratio corresponding to a predetermined first compression pressure in the characteristic line and the cumulatively added pulse wave value ratio corresponding to a second compression pressure that differs from the first compression pressure in the characteristic line, or a ratio of a compression pressure corresponding to a predetermined first cumulatively added pulse wave value ratio in the characteristic line and a compression pressure corresponding to a predetermined second cumulatively added pulse wave value ratio in the characteristic line;

visually displaying on a display a graph and a mark, wherein the graph includes an axis indicating blood pressure and an axis indicating a blood vessel hardness index, and the mark shows a position in a plotting area of the graph defined by the estimated systolic blood pressure and the estimated blood vessel hardness index; and when the position defined by the estimated systolic blood pressure and the estimated blood vessel hardness index is in a certain region in the graph, displaying on the display a message, an image, or a graphical pattern for notifying of a suspicion of hidden risk of cardiovascular disease.

\* \* \* \* \*